(12) United States Patent
Bodner

(10) Patent No.: US 11,337,843 B2
(45) Date of Patent: May 24, 2022

(54) KNEE BRACE

(71) Applicant: Daryl Bodner, Millersville, PA (US)

(72) Inventor: Daryl Bodner, Millersville, PA (US)

( * ) Notice: Subject to any disclaimer, the term of this patent is extended or adjusted under 35 U.S.C. 154(b) by 33 days.

(21) Appl. No.: 16/948,493

(22) Filed: Sep. 21, 2020

(65) Prior Publication Data
US 2021/0085503 A1 Mar. 25, 2021

Related U.S. Application Data

(60) Provisional application No. 62/902,546, filed on Sep. 19, 2019.

(51) Int. Cl.
*A61F 5/01* (2006.01)

(52) U.S. Cl.
CPC .................... *A61F 5/0125* (2013.01)

(58) Field of Classification Search
CPC ............... A61F 5/01–013; A61F 5/058; A61F 5/05841–05875; A61F 2005/0132–0179; A41D 13/05; A41D 13/06; A41D 13/065; A63B 71/08; A63B 71/12; A63B 71/1225; A63B 2071/125; A63B 2071/1275; B25J 9/0006
See application file for complete search history.

(56) References Cited

U.S. PATENT DOCUMENTS

| 3,901,223 A | * | 8/1975 | May | A61F 5/0123 602/16 |
| 4,523,585 A | * | 6/1985 | Lamb | A61F 5/0123 602/16 |
| 4,603,690 A | * | 8/1986 | Skeen | A61F 5/0123 602/16 |
| 4,628,916 A | * | 12/1986 | Lerman | A61F 5/0123 602/16 |
| 4,723,539 A | * | 2/1988 | Townsend | A61F 5/0123 602/16 |
| 5,039,247 A | | 8/1991 | Young et al. | |
| 5,168,865 A | * | 12/1992 | Radcliffe | A61F 5/0123 602/16 |
| 5,286,250 A | * | 2/1994 | Meyers | A61F 5/0123 602/16 |
| 5,611,774 A | * | 3/1997 | Postelmans | A61F 5/0123 602/16 |

(Continued)

OTHER PUBLICATIONS

International Search Report on Patentability and Written Opinion of the International Searching Authority, dated Dec. 15, 2020, 14 pages.

*Primary Examiner* — Michelle J Lee
(74) *Attorney, Agent, or Firm* — BakerHostetler

(57) ABSTRACT

A knee brace includes a support module including a first body, a second body, and a hinge movably coupling the first body to the second body. The includes a pin on one of the first and second bodies, and a receptacle on the other of the first and second bodies. The receptacle is configured to receive the pin therein, such that the pin is rotatable and translatable within the receptacle. The knee brace also includes a fastener configured to releasably attach the knee brace to a leg. One of the first and second bodies couples with a first portion of the leg via the fastener, and the other of the first and second bodies couples with a second portion of the leg via the fastener. The first and second portions of the leg are separated by a knee joint of the leg.

18 Claims, 35 Drawing Sheets

(56) References Cited

U.S. PATENT DOCUMENTS

| | | |
|---|---|---|
| 2005/0209545 A1 | 9/2005 | Farrow et al. |
| 2015/0290010 A1 | 6/2015 | Nace |
| 2015/0285287 A1* | 10/2015 | Jenkins, III ............... B32B 3/08 428/76 |
| 2017/0119569 A1 | 5/2017 | Hsu et al. |

* cited by examiner

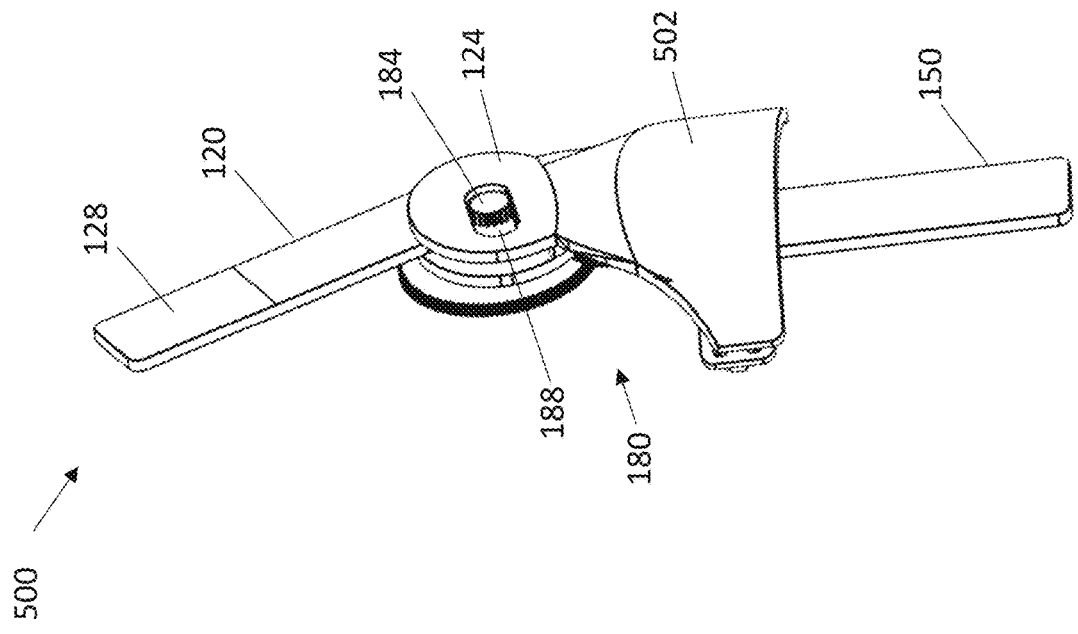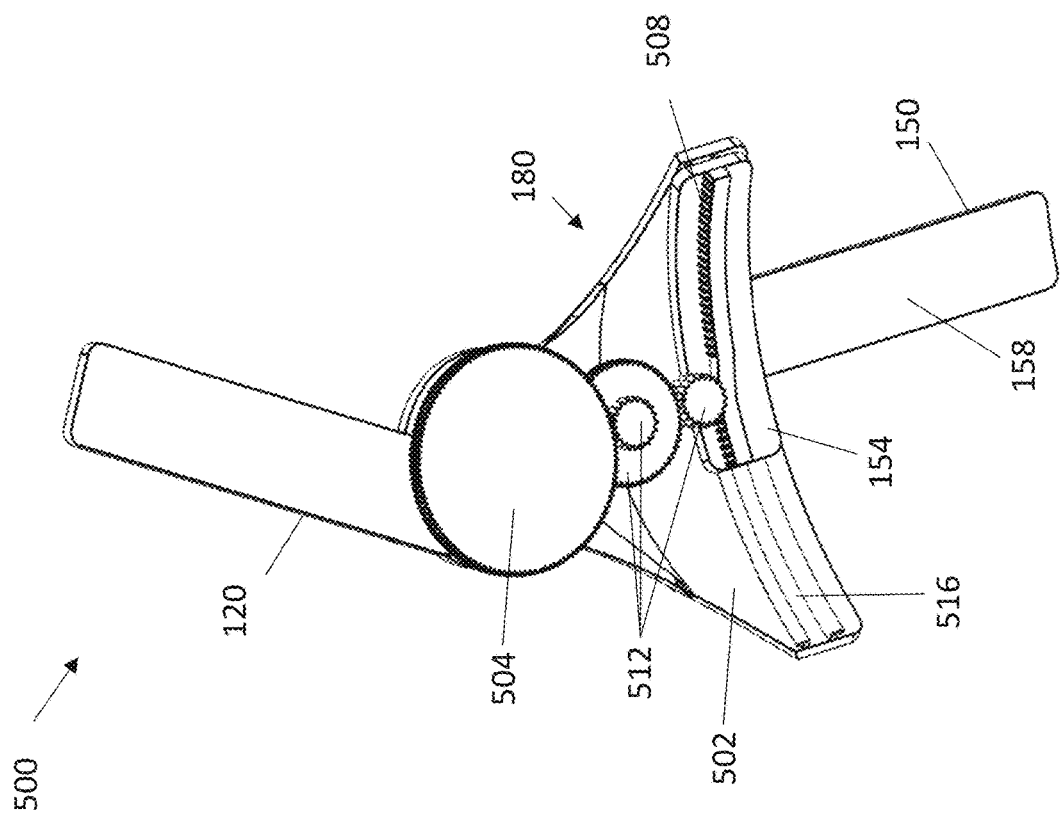

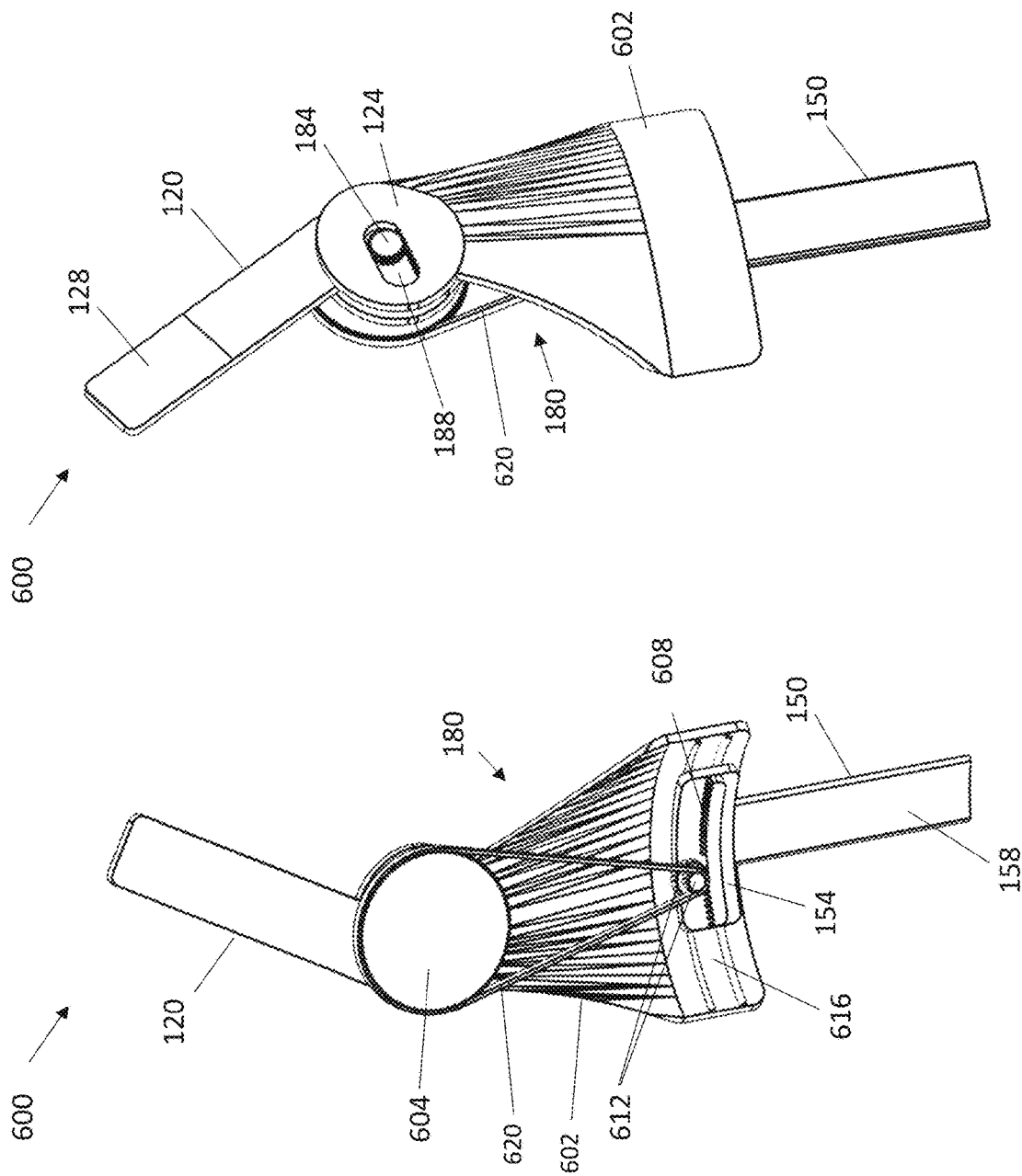

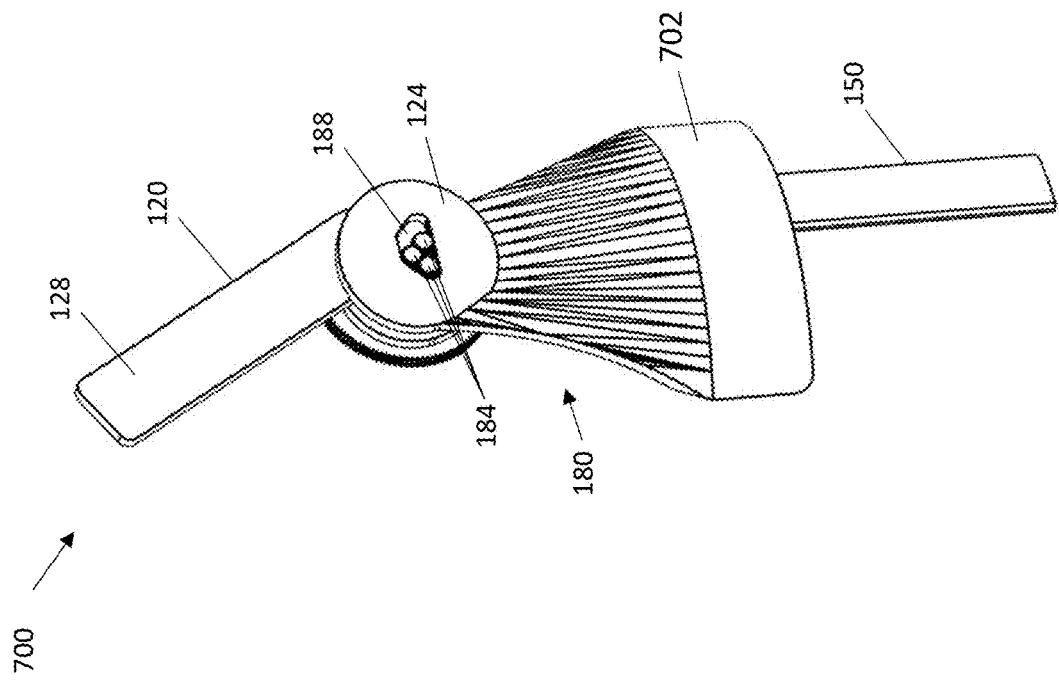
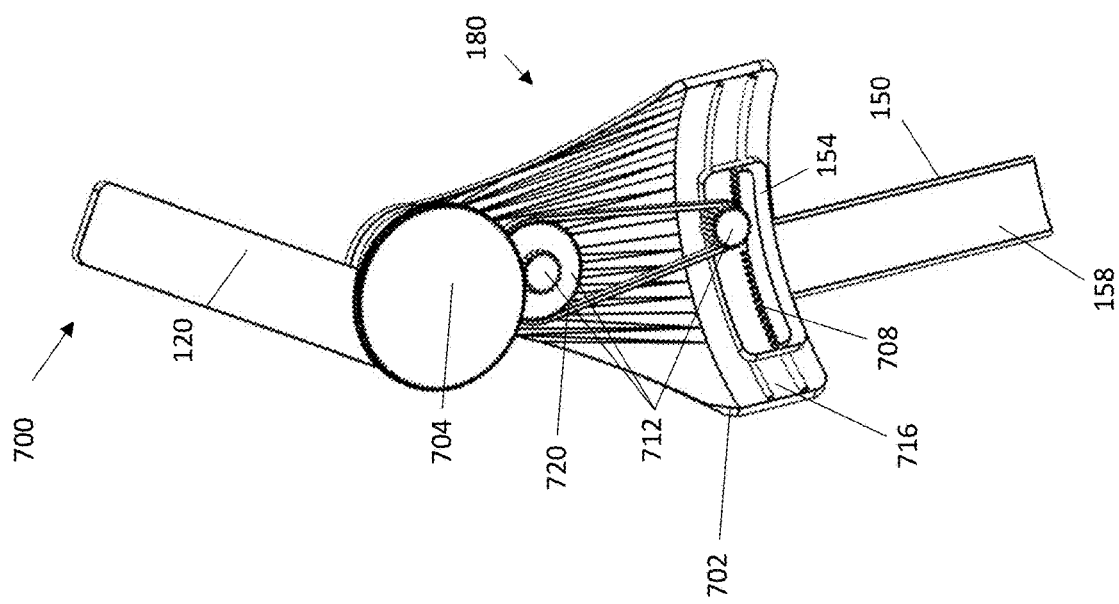
FIG. 22B
FIG. 22A

KNEE BRACE

CROSS REFERENCE TO RELATED APPLICATIONS

This application claims the benefit of U.S. Provisional Application No. 62/902,546, filed Sep. 19, 2019, the entirety of which is incorporated by reference herein.

TECHNICAL FIELD

This disclosure generally relates to devices and methods of supporting knee joints, and more particularly relates to knee braces that complements natural anatomical motion of the knee.

BACKGROUND

The human knee is constructed, in part, of two articulating long bones, the femur and the tibia, as well as several major ligaments, namely the collateral and cruciate ligaments, which serve to stabilize the knee joint from translational, rotational, and valgus and varus stresses. The particular curvatures of the bones, as well as the attachment sites of the ligaments, dictate the relative position of the tibia to the femur along the range-of-motion path of the knee joint between a fully flexed knee and a fully extended knee. Due to the specific geometries of individual bones, ligaments, and articulating surfaces, the knee joint does not function as a simple rotational hinge, and instead follows a complex pathway, defining rotations and translations along various axes.

Existing knee braces for supporting a knee joint operate as simple hinges. Such knee braces thus do not follow the natural anatomical flexion-extension path of the knee joint. Instead, the non-anatomical simple-hinge joint applies stresses to the bones and ligaments of the knee joint to force the knee to move in a simple-hinge fashion. This adversely affects comfort of wearing a knee brace, can lead to injury of the knee joint due to the non-anatomical stresses being forced on the knee, and can lead to other problems associated with incorrect knee movement, such as bad posture, pain, non-healing, or decreased mobility. As such, there is a need for an improved knee brace that provides necessary support to the knee joint while also conforming to an anatomically correct flexion-extension motion pathway.

SUMMARY

The foregoing needs are met by the various embodiments of knee braces disclosed. A knee brace includes a support module including a first body, a second body, and a hinge movably coupling the first body to the second body. The hinge includes a pin on one of the first and second bodies, and a receptacle on the other of the first and second bodies. The receptacle is configured to receive the pin therein, such that the pin is rotatable and translatable within the receptacle. The knee brace also includes a fastener configured to releasably attach the knee brace to a leg. One of the first and second bodies couples with a first portion of the leg via the fastener, and the other of the first and second bodies couples with a second portion of the leg via the fastener. The first and second portions of the leg are separated by a knee joint of the leg.

Optionally, the receptacle may be defined by a front wall, a rear wall opposite the front wall, a top wall, and a bottom wall opposite the top wall, the pin being slidably movable within the receptacle between the front, rear, top, and bottom walls. In some aspects, the front wall of the receptacle may be configured to contact the pin so as to prevent translational movement of the pin in a first direction, and the rear wall of the receptacle is configured to contact the pin so as to prevent translational movement of the pin in a second direction opposite the first direction.

Optionally, the first body may be configured to be translated along the hinge at a distance between 0 mm and 40 mm relative to the second body.

Optionally, the first body may be configured to be pivoted around the hinge between 0 degrees and 150 degrees relative to the second body.

Optionally, the support module may be a first support module configured to contact a lateral side of the leg, the knee brace further comprising a second support module configured to contact a medial side of the leg. In some aspects, the hinge may have a first configuration, in which the pin is disposed at a first position within the receptacle, and a second configuration in which the pin is disposed at a second position within the receptacle, the second position being rotationally and translationally offset from the first position. In some aspects, the hinge may be transitioned from the first configuration to the second configuration, the pin on one of the first and second support modules is moved within the receptacle of the one of the first and second support modules by a first distance, and the pin on the other of the first and second support modules is moved within the receptacle of the other of the first and second support modules by a second distance, the first distance being different from the second distance. In some aspects, when the hinge is transitioned from the first configuration to the second configuration, the second body of the first support module may be pivoted relative to the first body of the first support module along a first axis, the second body of the first support module may be configured to translate relative to the first body of the first support module at a first predetermined rate of distance per unit rotation, the second body of the second support module may be configured to translate relative to the first body of the second support module at a second predetermined rate of distance per unit rotation, and the first and second predetermined rates may be different from each other, such that the second leg portion is rotated along a second axis that is angularly offset from the first axis.

Optionally, the pin may define a plurality of teeth thereon, the receptacle defines a plurality of teeth therein, and the teeth on the pin are configured to engage with the teeth in the receptacle. In some aspects, the knee brace can further include a plurality of pins having pluralities of teeth thereon, each of the plurality of pins being configured to engage with a different set of plurality of teeth within the receptacle.

Optionally, each of the first and second bodies may define inhibitor surfaces configured to contact each other, such that when the inhibitor surfaces are in contact with each other, relative rotation between the first and second bodies is prevented in at least one rotational direction.

Optionally, the brace may further comprise a sleeve disposed between the first and second bodies and the leg, the sleeve comprising a deformable material configured to be compressed by the leg. In some aspects, the sleeve may include a plurality of tiles, wherein at least some of the plurality of tiles are movably coupled to each other. In some aspects, the plurality of tiles may be configured to be moved relative to each other in a first direction and configured to resist movement relative to each other in a second direction perpendicular to the first direction.

Optionally, the hinge may further include a hinge wall defining a curved channel thereon, the curved channel being configured to slidably receive the second body therein, wherein movement of the first body causes slidabe movement of the second body within the curved channel. In some aspects, the support module may be a first support module configured to contact a lateral side of the leg, the knee brace may further include a second support module configured to contact a medial side of the leg, wherein the first body of each of the first and second support modules is configured to be pivoted around a first axis between 0 degrees and 150 degrees relative to the second body of each respective first and second support module, and wherein the second body of each of the first and second support modules is configured to slidably translate along the curved channel of each respective first and second support modules, such that the second body of each of the first and second support modules is rotated, parallel to each other, along a second axis perpendicular to the first axis.

In some aspects, the pin may define a plurality of teeth extending circumferentially around at least a portion of the pin, and the lower body defines a rack having a plurality of teeth extending therefrom, the teeth on the pin being configured to contact the teeth on the rack in a geared engagement, wherein the rack has a first portion, a second portion adjacent the first portion, and a third portion adjacent the second portion, such that the second portion is disposed between the first and third portions, and the first and third portions being separated by the second portion, and wherein the second portion is devoid of the teeth on the rack. In some aspects, the second portion of the rack may define an incline separating the first portion from the third portion, such that a straight line extending along the first portion from the first portion to the second portion is offset from a parallel line extending along the third portion from the second portion through the third portion.

According to another aspect, a hinge for a knee brace includes a pin on one body; and a receptacle on another body, the receptacle being configured to receive the pin therein. The hinge is configured to transition from a first configuration in which the pin is disposed at a first position within the receptacle to a second configuration in which the pin is disposed at a second position within the receptacle, the second position being rotationally and translationally offset from the first position.

Optionally, the pin may define a plurality of teeth thereon, the receptacle defines a plurality of teeth therein, and the teeth on the pin are configured to engage with the teeth in the receptacle.

BRIEF DESCRIPTION OF THE DRAWINGS

The present application is further understood when read in conjunction with the appended drawings. For the purpose of illustrating the subject matter, the drawings show exemplary aspects of the subject matter; however, the presently disclosed subject matter is not limited to the specific methods, devices, and systems disclosed. In the drawings:

FIG. 20A depicts a perspective view of a support member for a knee brace according to yet another aspect of the disclosure;

FIG. 20B depicts another perspective view of the support member of FIG. 20A;

FIG. 21A depicts a perspective view of a support member for a knee brace according to yet another aspect of the disclosure;

FIG. 21B depicts another perspective view of the support member of FIG. 21A;

FIG. 22A depicts a perspective view of a support member for a knee brace according to yet another aspect of the disclosure;

FIG. 22B depicts another perspective view of the support member of FIG. 22A;

Aspects of the disclosure will now be described in detail with reference to the drawings, wherein like reference numbers refer to like elements throughout, unless specified otherwise.

DETAILED DESCRIPTION OF ILLUSTRATIVE EMBODIMENTS

Figure 1:
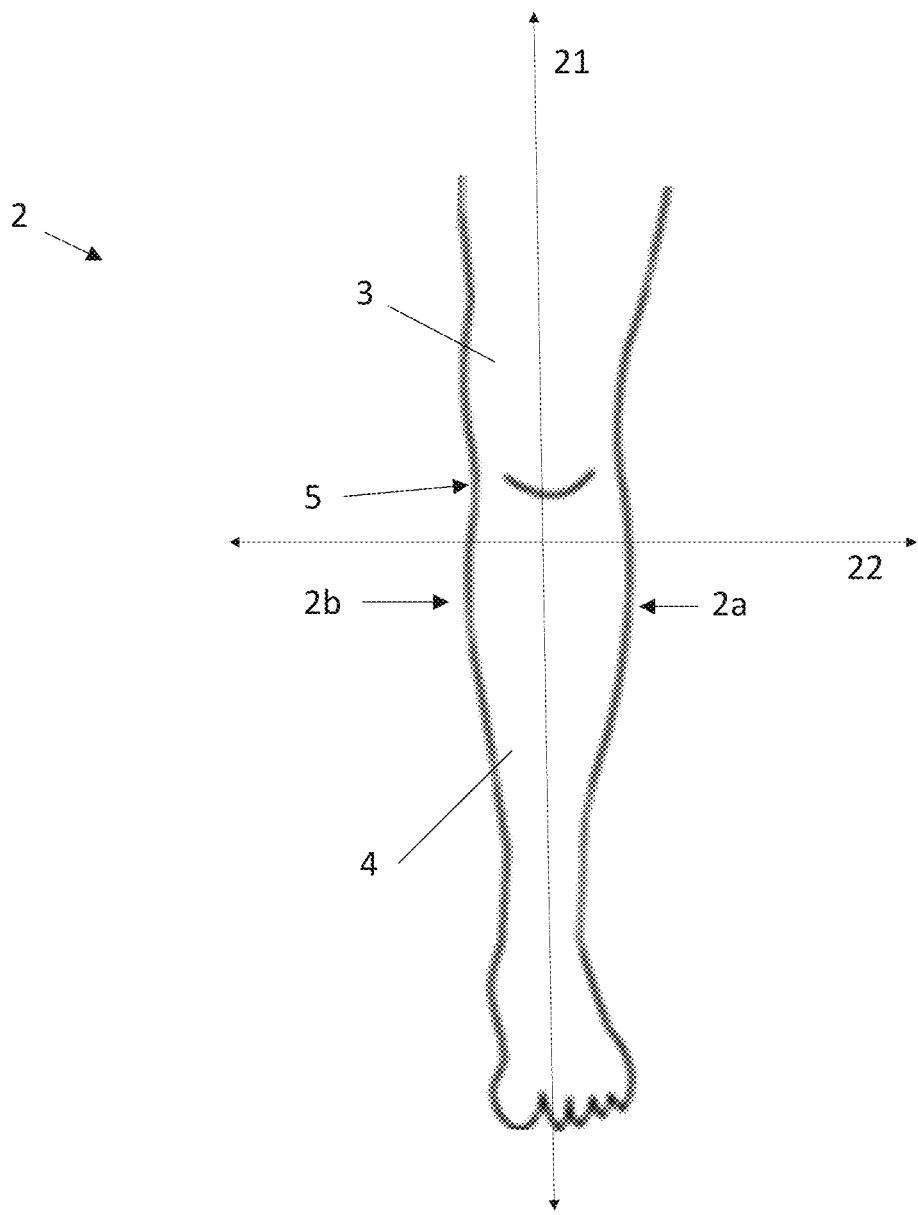
FIG. 1 depicts a front perspective view of a human leg showing coordinates referenced throughout this disclosure.

For purposes of this disclosure, relative directions and planes will be described either with reference to a first coordinate system defined by a first portion of a human leg or with reference to a second coordinate system defined by a second portion of the human leg that is configured to move relative to the first portion of the leg. Referring to FIGS. 1-4, a human leg 2 is shown having an upper leg portion 3 and a lower leg portion 4 separated by a knee joint 5. It will be understood that the femur bone is disposed, at least in part, in the upper leg 3, and the tibia bone is disposed, at least in part, in the lower leg 4. The knee joint 5 includes articulating portions of both the femur and the tibia bones. An upper frontal axis 21 extends through the leg 2 from the upper leg 3 to the lower leg 4. An upper transverse axis 22 extends across the leg 2 from a lateral side 2a of the leg 2 to a medial side 2b opposite the lateral side 2a. The lateral side 2a is separated from the medial side 2b by the upper frontal axis 21. An upper sagittal axis 23 extends across the leg 2 from a front (anterior) side 2c of the leg 2 to a rear (posterior) side 2d of the leg 2. The anterior side 2c is separated from the posterior side 2d by the upper frontal axis 21 and the upper transverse axis 22. The upper sagittal axis 23 is perpendicular to both the upper frontal and upper transverse axes 21 and 22.

Figure 2:
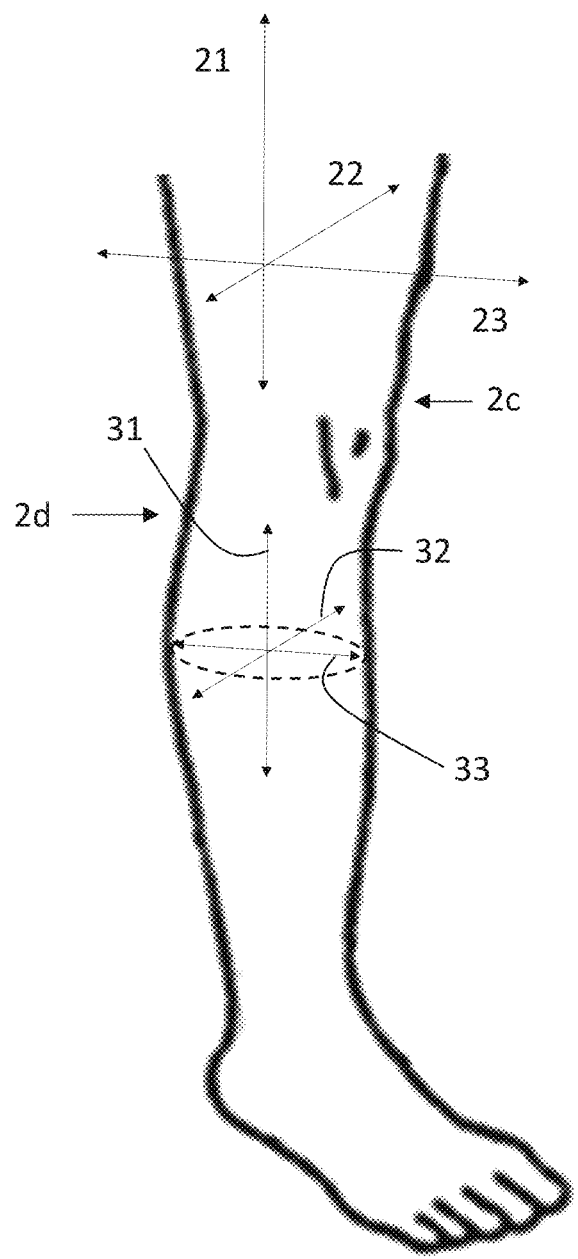
FIG. 2 depicts a perspective view of the human leg of FIG. 1 showing more coordinates references throughout this disclosure.
Figure 3:
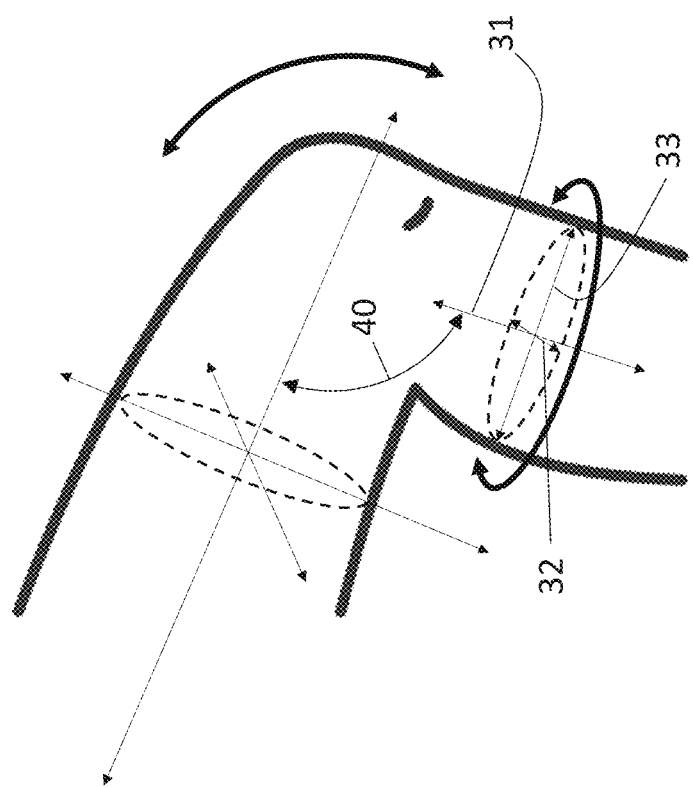
FIG. 3 depicts a perspective view of the human leg of FIG. 1 showing a flexed knee.
Figure 4:
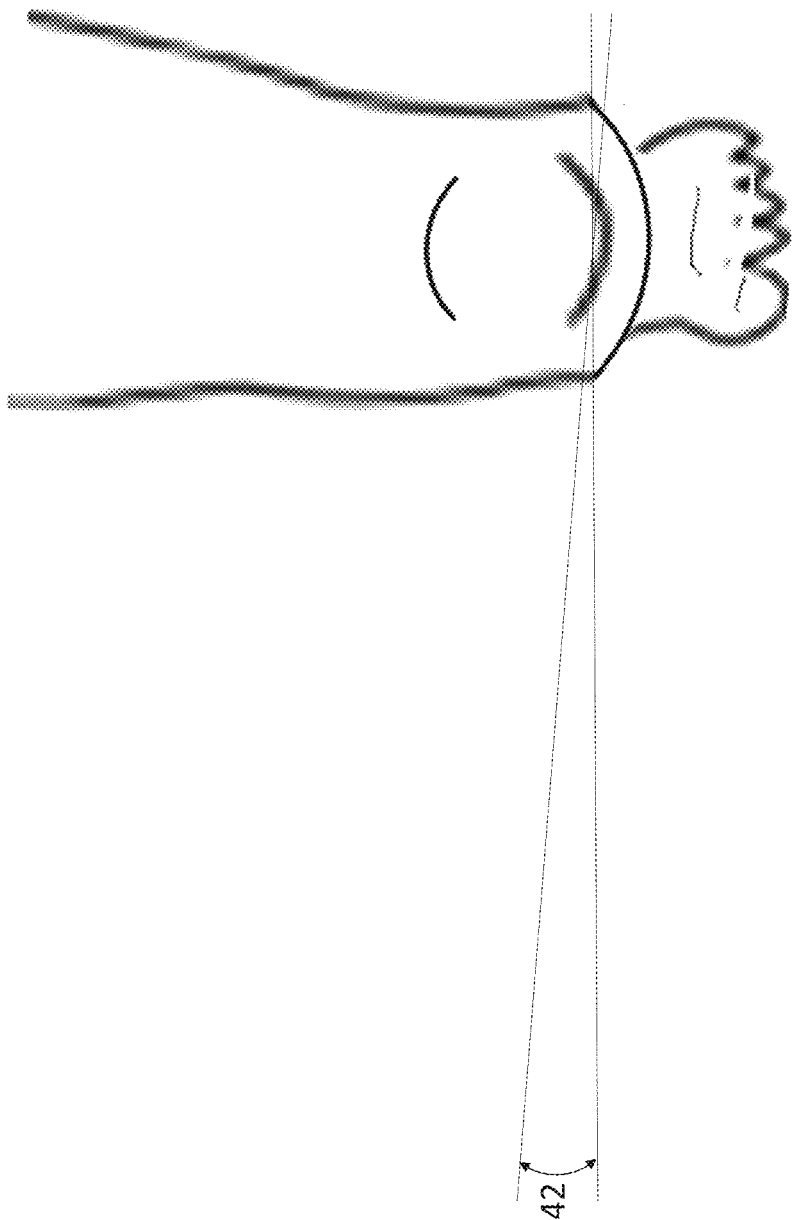
FIG. 4 depicts a front perspective view of the human leg of FIG. 1 showing a flexed knee.

A second coordinate system will be used to refer to the lower portion of the leg 2 that is below the knee joint 5. Referring to FIGS. 2 and 3, a lower frontal axis 31 extends through the leg 2 from the lower leg portion 4 to the knee joint 5. A lower transverse axis 32 extends across the lower leg 2 between the lateral side 2a and the medial side 2b. A lower sagittal axis 33 extends through the lower leg 4 from the anterior side 2c to the posterior side 2d. When the leg 2 is in an extended position (see FIGS. 1 and 2), the upper and lower frontal axes 21 and 31 may be parallel to each other. In some orientations of the leg 2, between full flexion and full extension, the lower transverse axis 32 may be parallel to the upper transverse axis 22, and the upper and lower sagittal axes 23 and 33 may be parallel to each other. When the leg 2 is in a flexed position (see FIGS. 3 and 4), the upper and lower frontal axes 21 and 31 are angularly offset from each other along an angle 40. In the flexed position, the lower transverse axis 32 is angularly offset from the upper transverse axis 22 by an axial angle 42 (see FIG. 4). The position of the lower leg 4 will be described relative to the position of the upper leg 3. Flexion will refer to a movement that decreases the angle 40 between the upper leg 3 and the lower leg 4; extension will refer to a movement opposite of flexion that increases the angle 40 between the upper leg 3 and the lower leg 4. Reference to the above directions will be used throughout this application.

Figure 5:
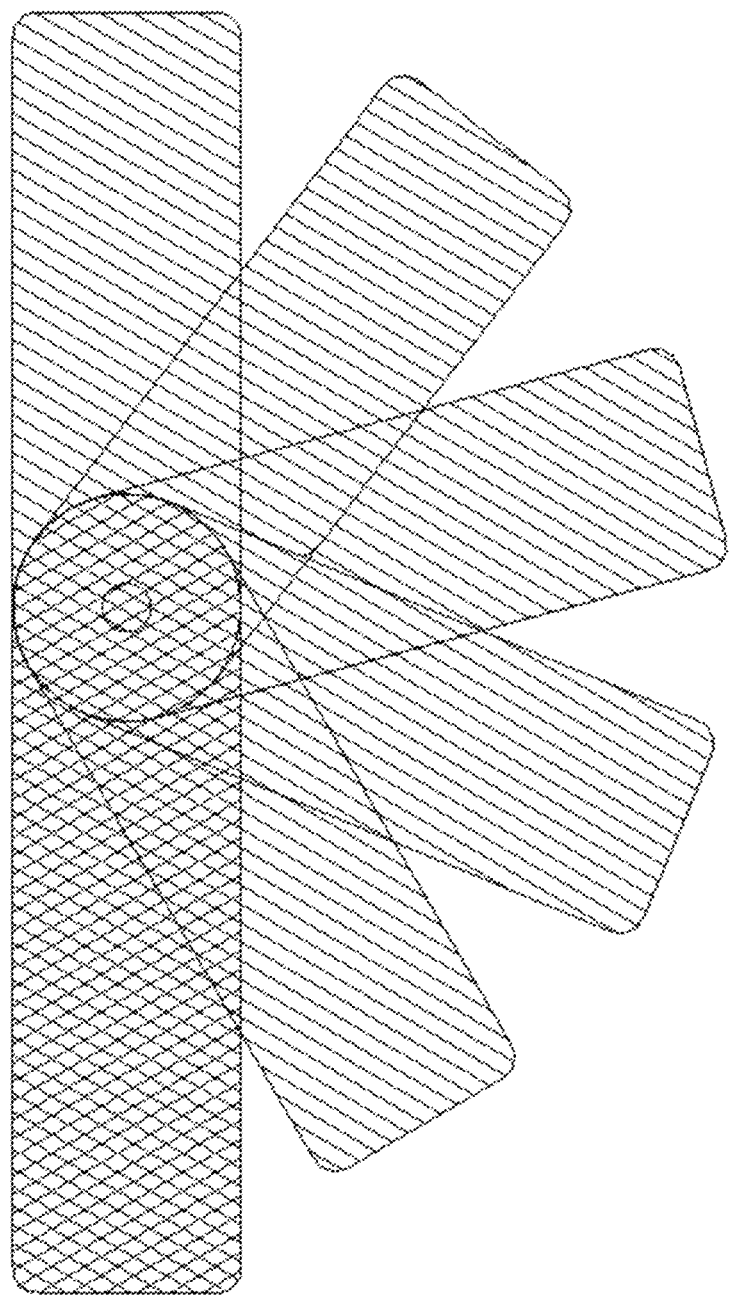
FIG. 5 depicts a prior art knee brace.

Existing knee braces typically operate as simple hinges. In such braces is, a first, top portion of the brace is attached to the upper leg of the wearer above the knee joint, and a second, lower portion is attached to the lower leg of the wearer below the knee joint. As shown in the side-view schematic of FIG. 5, these top and bottom portions are connected to each other at a simple rotational hinge adjacent to the knee joint between the top and bottom portions of the brace. During flexion and extension, the top and bottom portions rotate relative to each other around the hinge that connects the portions. However, such braces do not account for various other translations and rotations of the knee joint. For example, in addition to rotation along a hinge in a plane defined by the upper frontal axis 21 and the upper sagittal axis 23 (i.e. to increase or decrease the flexion angle 40), the lower leg 4 (i.e. below the knee joint 5) also moves relative to the upper leg 3 (i.e. above the knee joint 5) in a translational motion in the plane defined by the frontal and sagittal axes 21 and 23. Furthermore, the lower leg 4 also rotates along the lower frontal axis 31, relative to the upper frontal axis 21, such that the axial angle 42 is varied in different positions between full extension and full flexion of the leg 2. Accordingly, existing knee braces do not offer support in all of the rotational and translational directions of the knee. Moreover, by allowing motion only around a single rotational point in the sagittal plane, such existing braces further limit the range of motion of the knee joint and can lead to injury.

Figure 6:
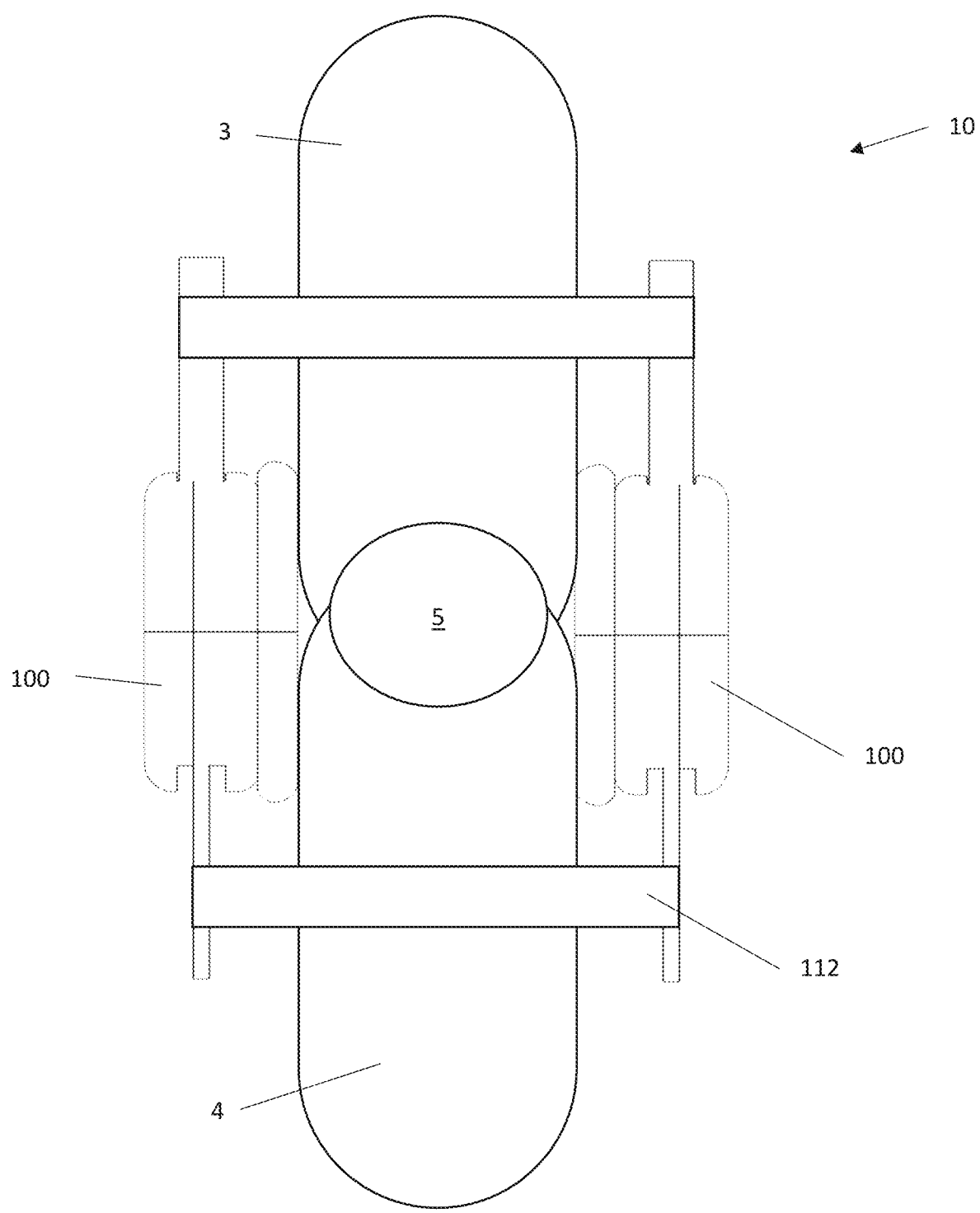
FIG. 6 depicts a knee brace according to an aspect of this disclosure.

Referring to FIG. 6, a knee brace 10 is disclosed that provides support in a plurality of rotational and translational motions of the knee joint between full flexion and full extension. The knee brace 10 is configured to releasably couple to a leg 2 of the wearer. The knee brace 10 attaches to the upper leg 3 and to the lower leg 4 separated from the upper leg 3 along the upper frontal axis 21. The knee joint 5 is disposed between the upper leg 3 and the lower leg 4 and separates the upper and lower legs 2 and 3. The knee brace 10 includes at least one support module 100. The support module 100 is configured to contact the leg 2 at the lateral side 2a of the leg 2 or at the medial side 2b of the leg 2. In some embodiments, the knee brace 10 may include two support modules 100, where one of the two support modules 100 is disposed adjacent the lateral side 2a of the leg 2 while the other of the two support modules 100 is disposed adjacent the medial side 2b of the leg 2. Each support module 100 has a first side 104 configured to contact the leg 2. A second side 108 is defined on the support module 100 opposite the first side 104. A fastener 112 is configured to removably affix the support module 100 to the leg 2. The fastener 112 may be disposed between the leg 2 and each support module 100. The knee brace 10 may include a plurality of fasteners 112. In some embodiments, the fastener 112 may be an elastic strap configured to be stretched around the wearer's leg. In other embodiments, the fastener 112 may be a hook-and-loop strap configured to be looped and releasably locked around the wearer's leg. In some embodiments, the fastener 112 may include a sleeve configured to receive a portion of each module 100 therein and to secure each module 100 to the leg 2. For example, embodiments of such fasteners are described further below.

Figure 7:
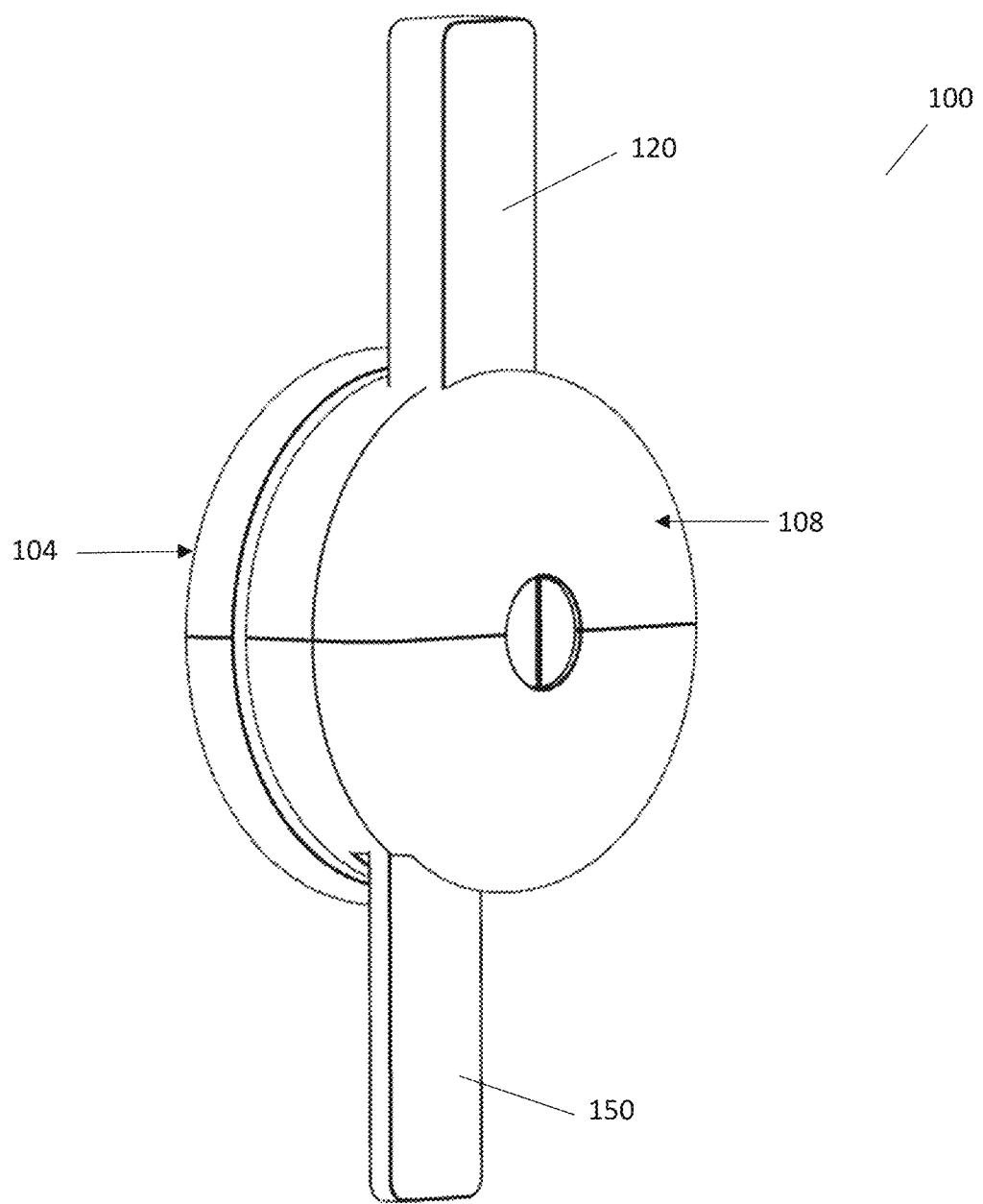
FIG. 7 depicts a support member of a knee brace according to an aspect of this disclosure.
Figure 8:
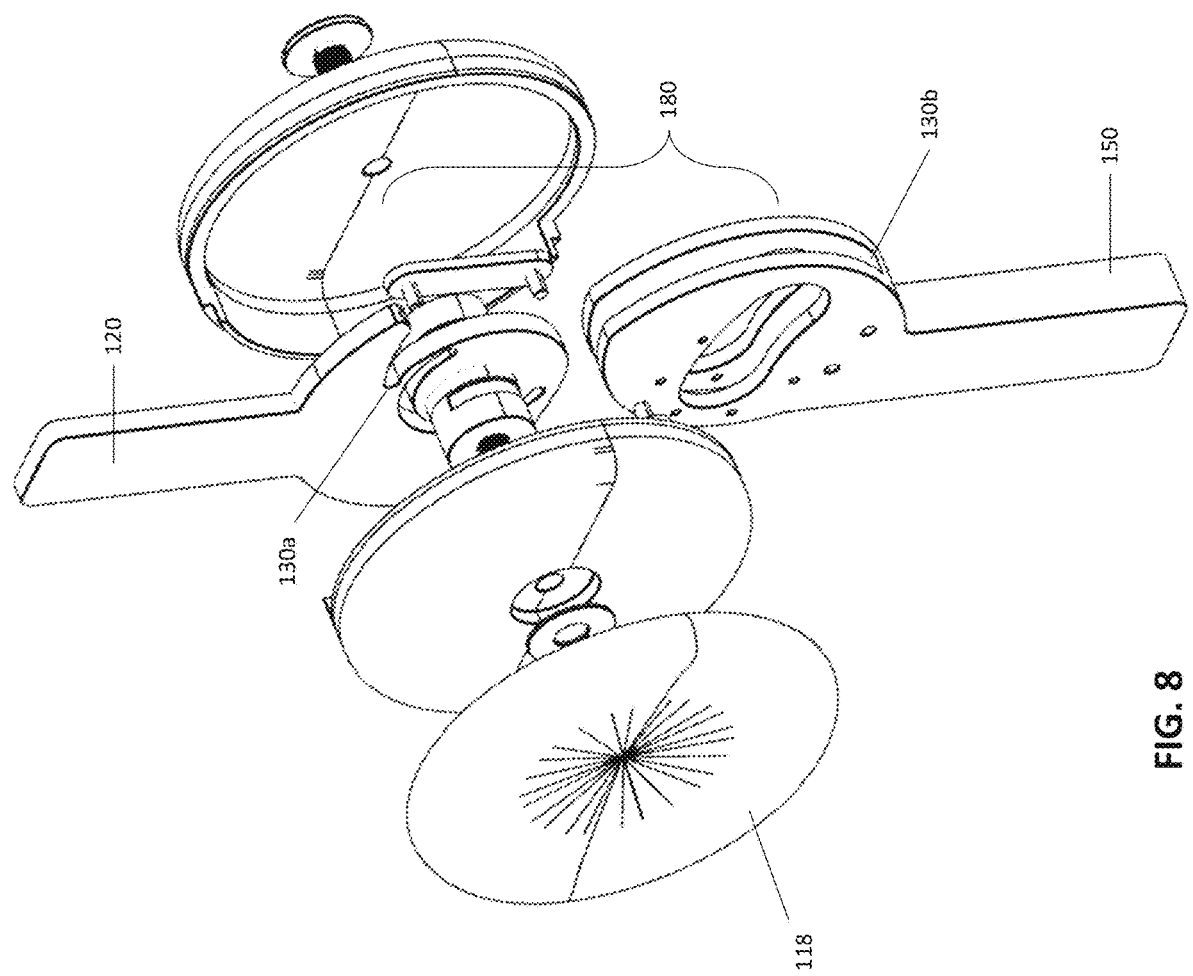
FIG. 8 depicts an exploded perspective view of the support member of FIG. 7.
Figure 9:
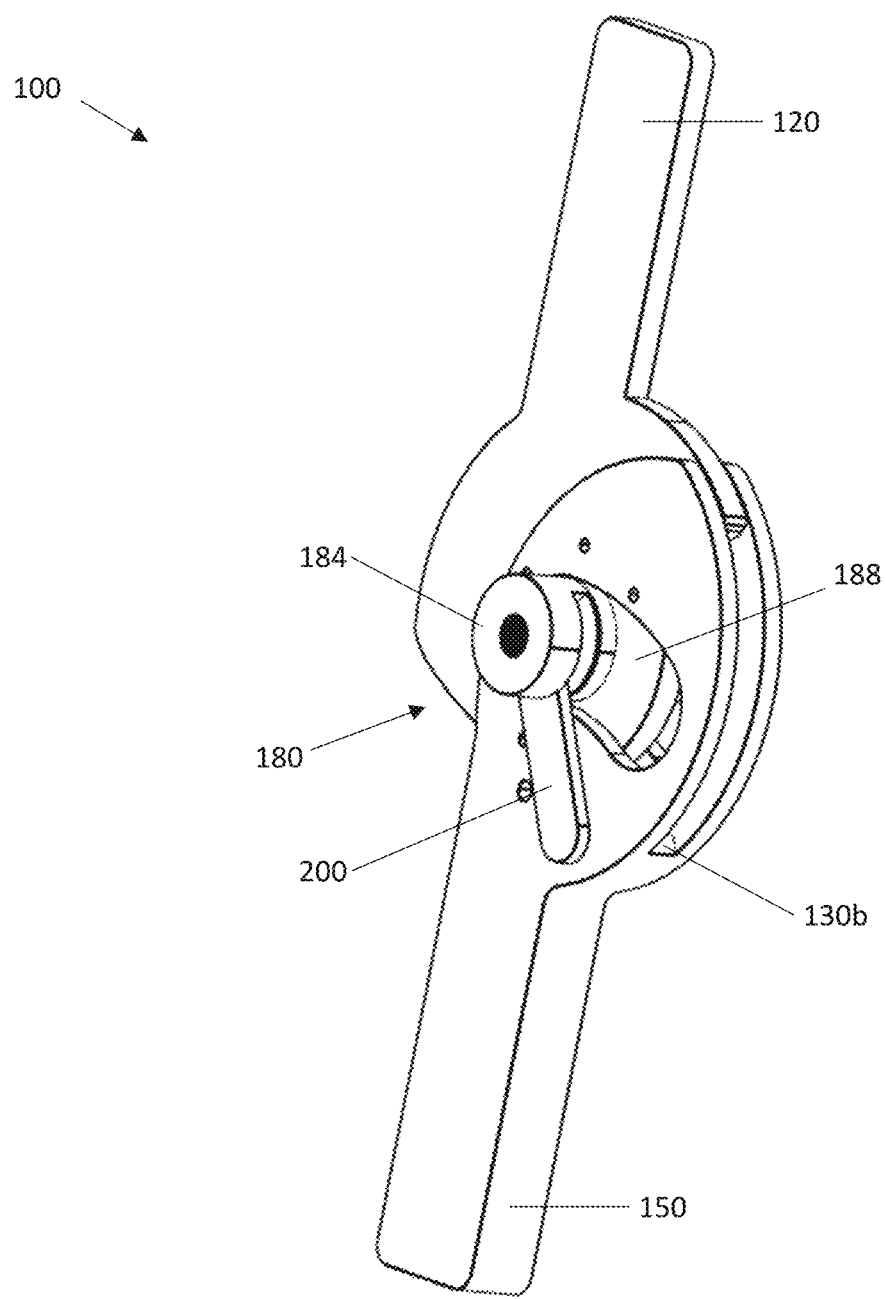
FIG. 9 depicts an angled perspective view support member according to another aspect of this disclosure.

Referring to FIGS. 7-9, the support module 100 includes a first body 120 and a second body 150 that is configured to be moved relative to the first body 120. A hinge 180 is defined between the first body 120 and the second body 150. The first and second bodies 120 and 150 are configured to be moved relative to each other along the hinge 180. The first body 120 may be configured to attach to the upper leg 3 while the second body 150 may be configured to attach to the lower leg 4. Alternatively, the first body 120 may be attachable to the lower leg 4 while the second body 150 may be attachable to the upper leg 3. This disclosure will refer to the first body 120 as attaching to the upper leg 3 and to the second body 150 as attaching to the lower leg 4, but it will be understood that the arrangement can be reversed, and this disclosure is not limited to the particular described arrangement above.

Figure 10A:
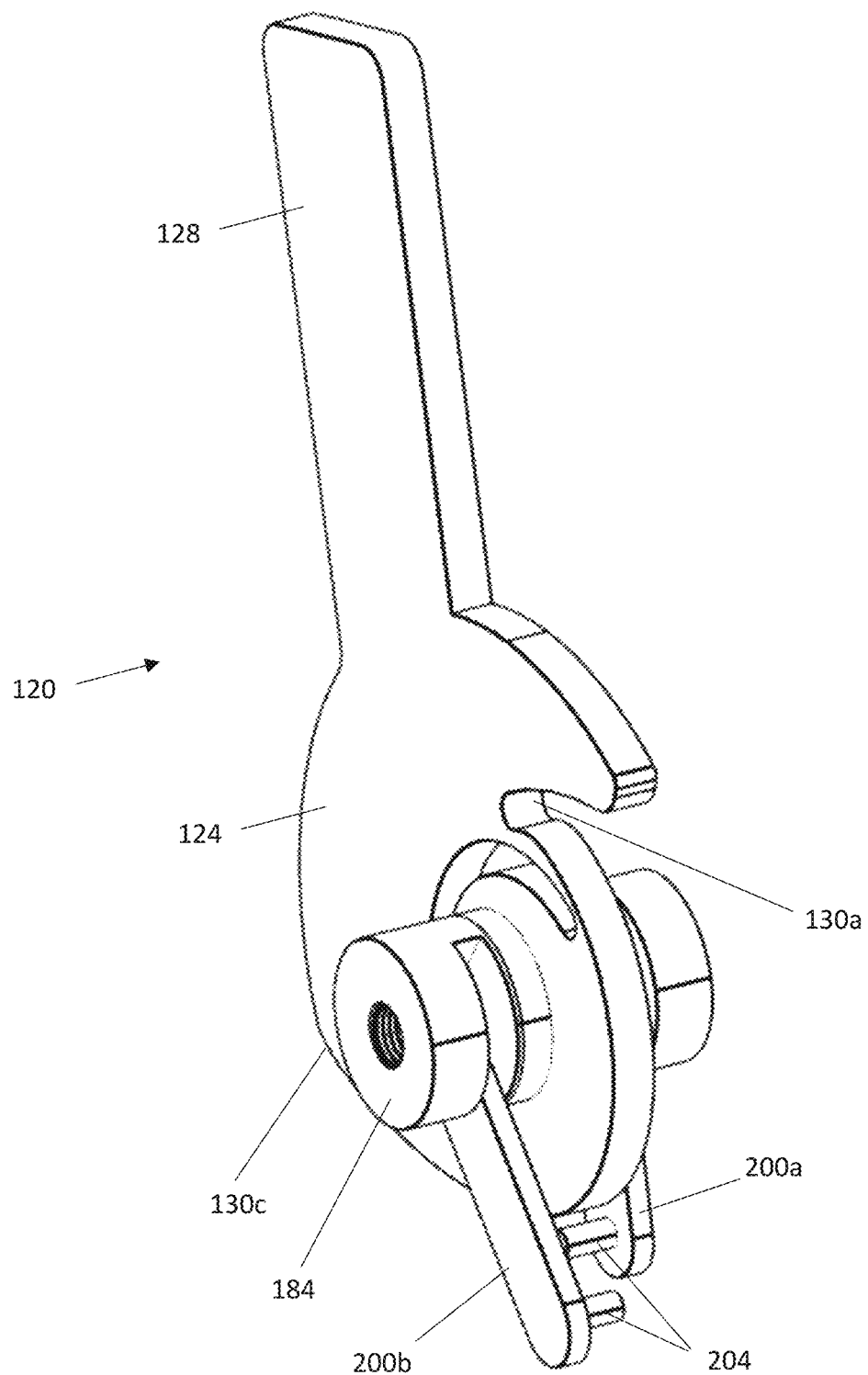
FIG. 10A depicts an angled perspective view of the first body of the support member of FIG. 9 according to an aspect of this disclosure.

Referring to FIG. 10, the first body 120 includes a head 124 connected to a neck 128 that extends from the head 124. The neck 128 may include, may receive, or may be received into or onto, one or more fasteners 112 configured to releasably affix the support module 100 to the leg. The head 124 may include a pin 184 extending therefrom. The pin 184 may be substantially cylindrical. The pin 184 is configured to engage with a recess 188 (see FIG. 11) as will be described below. The pin 184 may be smooth around its circumference, or may alternatively have teeth defined thereon circumferentially, such that the teeth can engage with complementary teeth in a geared engagement (as will be described with respect to an exemplary embodiment below).

Figure 11:
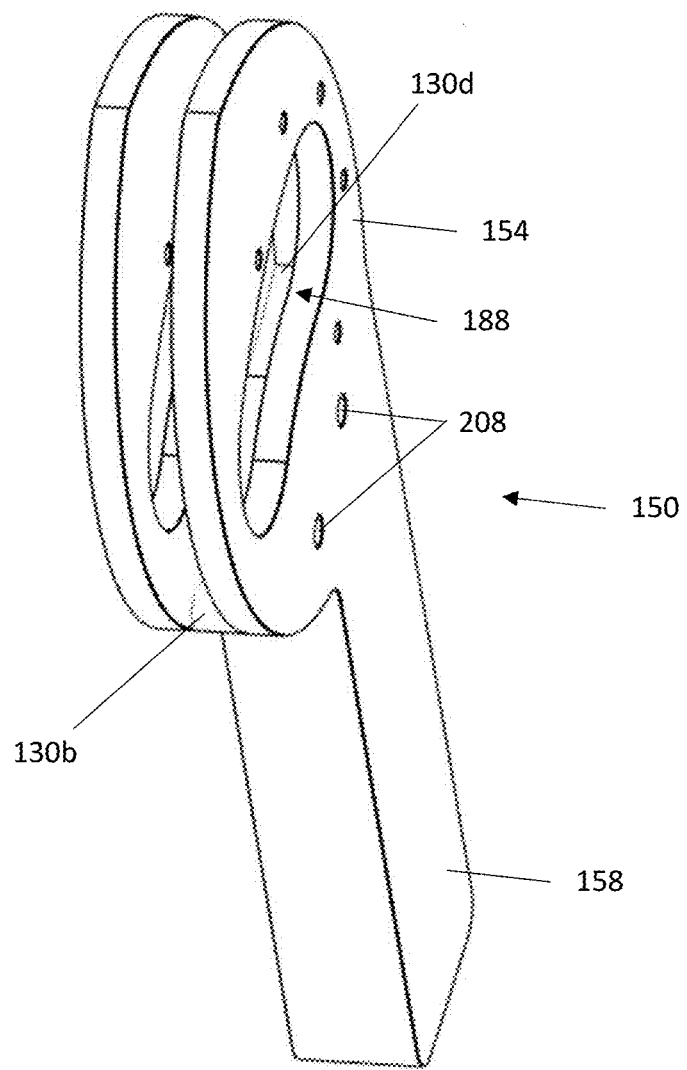
FIG. 11 depicts an angled perspective view of a second body of the support member of FIG. 9 according to an aspect of this disclosure.

Referring to FIG. 11, the second body 150 includes a head 154 connected to a neck 158 that extends from the head 154. The neck 158 may include, or may receive, one or more fasteners 112 configured to releasably affix the support module 100 to the leg. The head 154 includes a recess 188 configured to receive the pin 184 therein. The pin 184 is rotatable within the recess 188. In some aspects, the pin 184 is linearly translatable within the recess 188. Although the present disclosure depicts the pin 184 on the first body 120 and the recess 188 on the second body 150, it will be understood that this arrangement can be reversed.

The pin 184 and the recess 188 define a hinge 180 that operably connects the first body 120 with the second body 150. The first and second bodies 120 and 150 may pivot relative to each other around the hinge 180 (i.e. the pin 184 may rotate within the recess 188). In some aspects, the first and second bodies 120 and 150 may additionally translate relative to each other along the hinge 180 (i.e. the pin 184 may slide within the recess 188). The relative motion along the hinge 180 will be described in detail below.

The first body 120 may be further attached to the second body 150 by a support strut 200. A pin 204 extends from the support strut and is configured to be received into a circular notch 208 defined on at least one of the first body 120 and the second body 150 to movably connect the support strut 200 to each of the first and second bodies 120, 150. In some embodiments, the support strut 200 includes a pin 204 at one end thereof that is configured to be received into a notch 208 on the first body 120, and further includes a pin 204 at the other end thereof that is configured to be received into a notch 208 on the second body 150. The strut 200 has a length 202 (see FIG. 10B). The length of each strut 200, as well as the placement of notches 208, are not arbitrary and serve specific purposes.

Figure 10B:
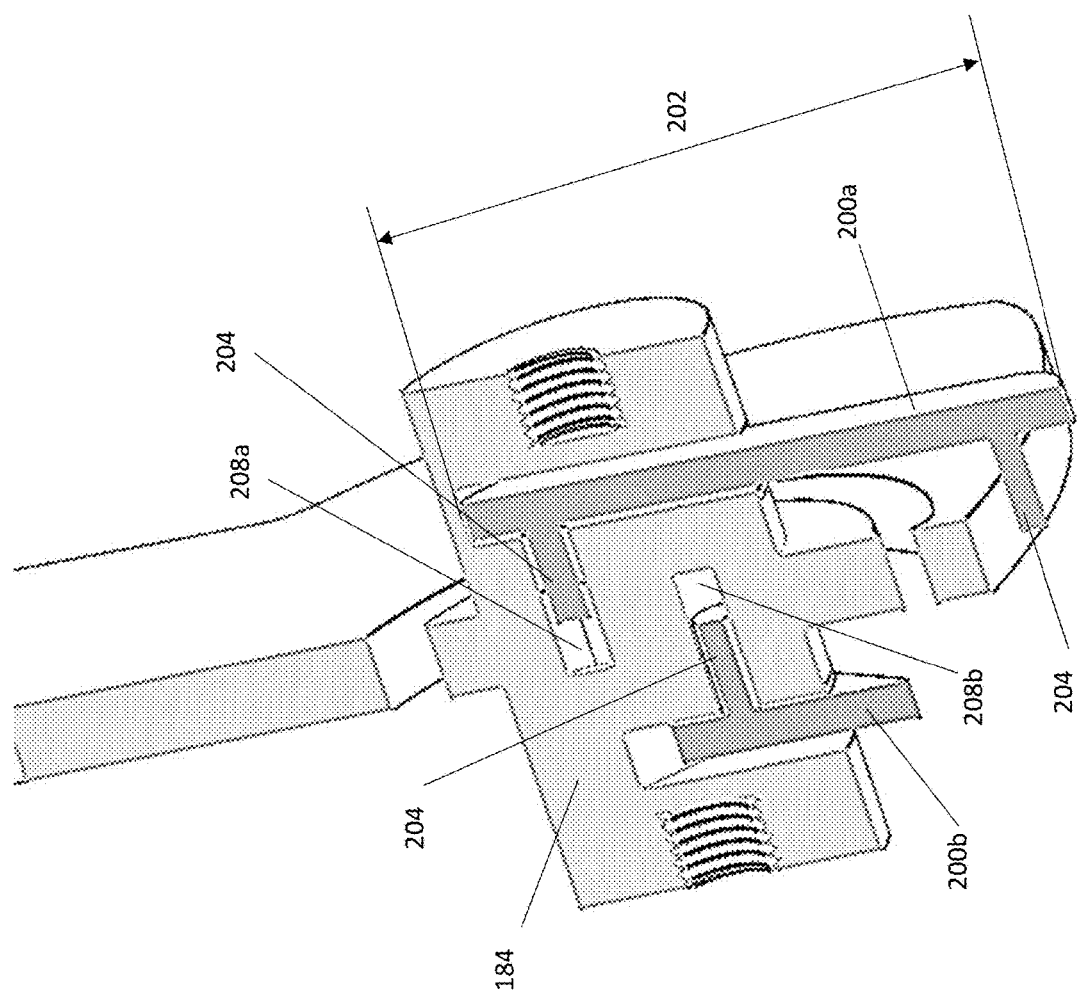
FIG. 10B depicts a cross-sectional angled perspective view of the first body of the support member of FIG. 9 according to an aspect of the disclosure.

The support strut 200 is configured to be rotationally movable, around the pin 204 within the notch 208, with respect to at least one of the first and second bodies 120 and 150. When the first and second bodies 120 and 150 move relative to one another around and/or along the hinge 180, the support strut 200 may serve as physical reinforcement for rotational and translational forces associated with the relative movement of the first and second bodies 120 and 150. The support strut 200 may further serve as a range-of-motion inhibitor to prevent rotation and/or translation of the first body 120 relative to the second body 150 outside of a predetermined range. Referring to FIG. 10, the support module 100 may include a first strut 200a and a second strut 200b. One of the first and second struts 200a and 200b is disposed on one side of the support module 100 (e.g. on the side contacting the leg of the wearer), and the other of the first and second struts 200a and 200b is disposed on the opposite side of the support module 100 (e.g. the side facing away from the wearer's leg). In operation, the first and second struts 200a and 200b may provide similar support for the first and second bodies 120 and 150 as is provided by the anterior cruciate ligament and the posterior cruciate ligament for the upper leg 3 and the lower leg 4 in an average human leg 2. In some embodiments, the first strut 200a may have a length 202 of between about 20 mm and about 30 mm; between about 22 mm and about 28 mm; between about 24 mm and about 27 mm; or another suitable range or combination of above ranges. In some embodiments, the length 202 of the first strut 200a may be about 26.5 mm. The second strut 200b may have a length 202 of between about 20 mm and about 30 mm; between about 22 mm and about 28 mm; between about 24 mm and about 27 mm; or another suitable range or combination of above ranges. In some embodiments, the length 202 of the second strut 200b may be about 26.75 mm. Each of the first and second struts 200a and 200b is hingedly inserted, via the pins 204 thereon, into respective notches 208 on the first body 120. The notches 208 on the first body 120 may be disposed within, on, or adjacent to the pin 184. Referring again to FIG. 10B, a first notch 208a is configured to receive the pin 204 from the first strut 200a, and a second notch 208b is configured to receive the pin 204 from the second strut 200b. In some embodiments, the first notch 208a may be disposed at a first predetermined distance from the center of the pin 184 (in a plane defined by the upper frontal axis 21 and the upper sagittal axis 23), while the second notch 208b may be disposed at a second predetermined distance from the center of the pin 184. The first distance may be different from the second distance. In some embodiments, the first distance for the first notch 208a from the center of the pin 184 may be between about 2 mm and about 5 mm; between about 2.5 mm and about 4.5 mm; between about 3 mm and about 4 mm; or another suitable distance or combination of ranges above. In some embodiments, the first distance may be about 3.5 mm. In some embodiments, the second distance for the second notch 208b from the center of the pin 184 may be between about 2 mm and about 5 mm; between about 2.5 mm and about 4.5 mm; between about 3 mm and about 4 mm; or another suitable distance or combination of ranges above. In some embodiments, the second distance may be about 4 mm. An angular offset between the first and the second notches 208a and 208b may be approximately 130 degrees. The length, angular separation, and locations of notches 208 for the struts 200 are not arbitrary and are calculated based on the desired locations of attachment on the tibial plateau based on natural human anatomy. During flexion and extension of the first body 120 relative to the second body 150, the rotation of the struts 200 follows causes movement of the struts 200 and the relative movement between the first and second bodies 120 and 150 to simulate epicycloid motion of the cruciate ligament attachment points on the femoral condyles in the human knee joint.

Figure 12:
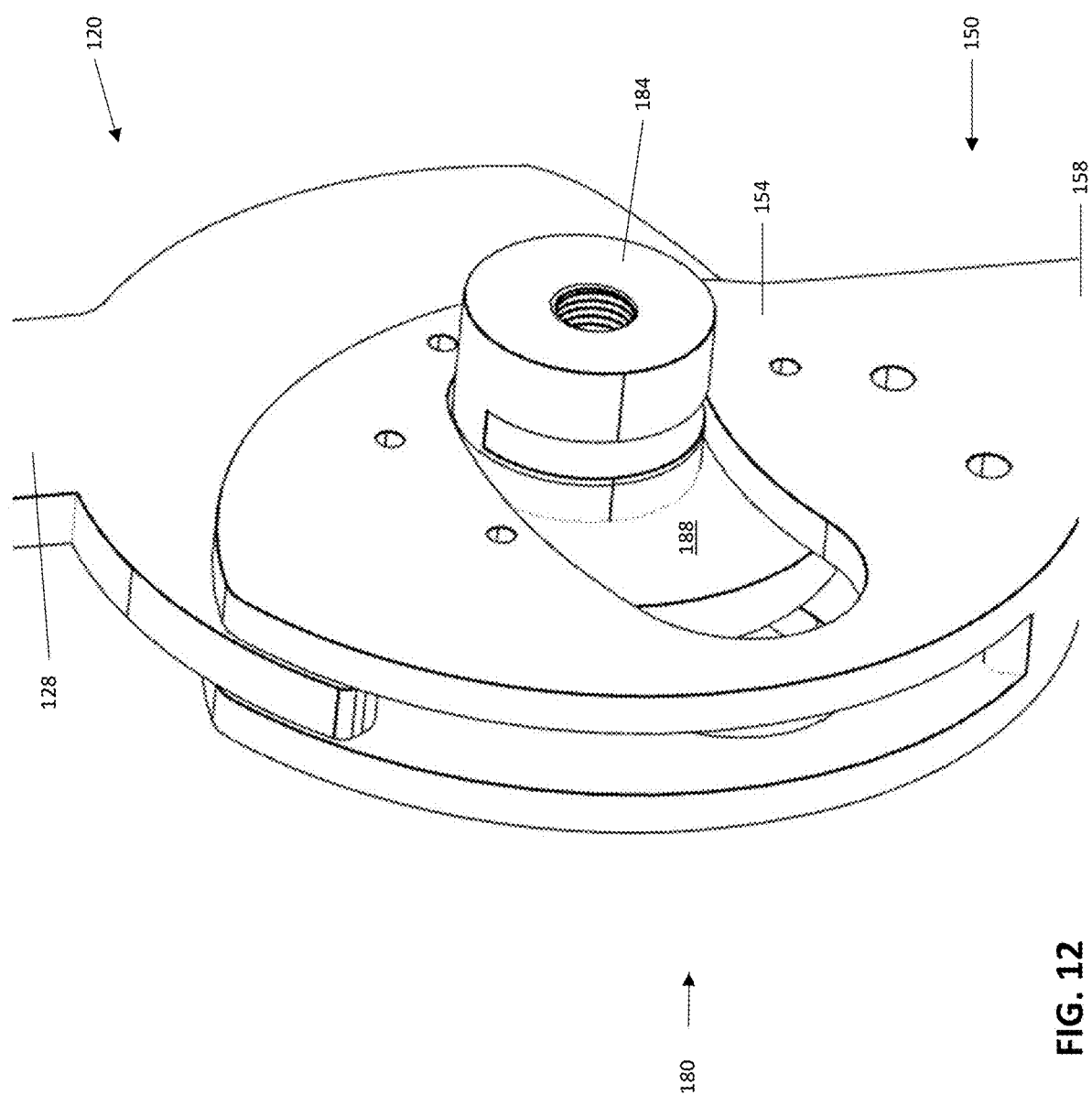
FIG. 12 depicts an angled perspective view of a portion of the support member of FIG. 9.
Figure 13:
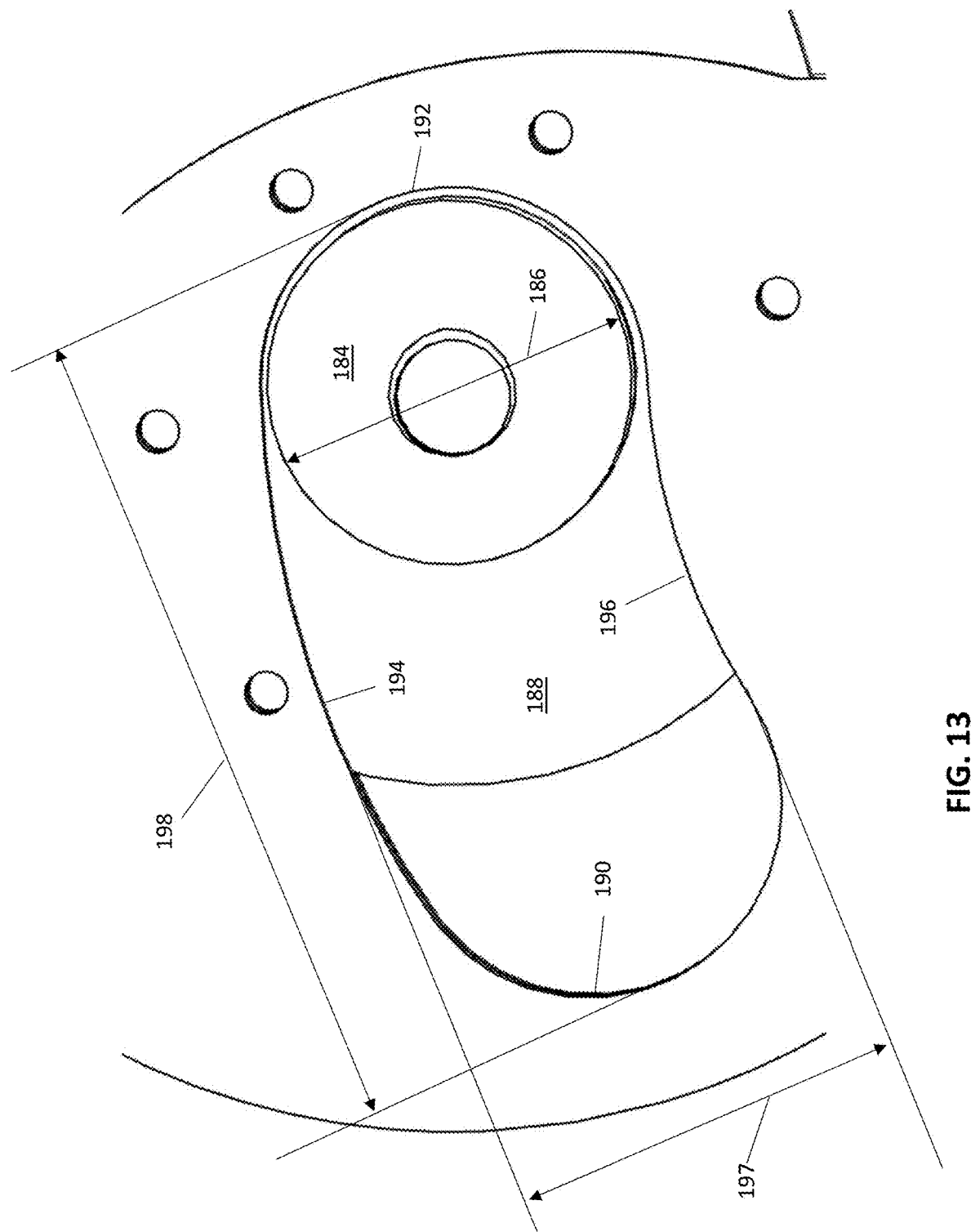
FIG. 13 depicts a side perspective view of a hinge of the support member of FIG. 9 according to an aspect of this disclosure.

Referring to FIGS. 12 and 13, the hinge 180 is shown in detail. The hinge 180 is defined between the first body 120 and the second body 150. In the depicted embodiment, the pin 184 is disposed on the first body 120, while the recess 188 is defined on the second body 150, but it will be understood that in alternative embodiments, the above arrangement can be reversed to have the pin 184 on the second body 150 and the recess 188 on the first body 120. The recess 188 may be defined by a front wall 190, a rear wall 192 opposite the front wall 190, a top wall 194, and a bottom wall 196 opposite the top wall 194. The recess 188 is dimensioned such the pin 184 can be disposed therein. In some embodiments, the recess 188 may be sized to allow the pin 184 to translate within the recess 188. The recess 188 defines a height 197, measured between the top wall 194 and the bottom wall 196, and a length 198, measured between the front wall 190 and the rear wall 192. The pin 184 may have a circular cross section and include a diameter 186. In some embodiments, the pin 184 may have a diameter 186 of between about 4 mm and about 20 mm; of between about 6 mm and about 18 mm; of between about 8 mm and about 16 mm; of between about 10 mm and about 14 mm; or a combination of the above ranges. In some embodiments, the diameter of the pin 184 may be approximately 16 mm. The height 197 of the recess 188 may be sufficiently large to receive the pin 184 therein but not large enough to allow translation of the pin 184 towards or away from the top and bottom walls 194 and 196. That is, the height 197 of the recess 188 may be only slightly larger than the diameter 186 of the pin 184. The length 198 of the recess 188 may be greater than the diameter of the pin 184, such that the pin 184 is movable within the recess 188 along the length 198 between the front wall 190 and the rear wall 192. In some embodiments, the length 198 may be between about the size of the diameter of the pin 184 and about 40 mm. In some embodiments, the recess 188 may be arcuate between the front wall 190 and the rear wall 192. That is, the top wall 194 and the bottom wall 196 may be curved between the front wall 190 and the rear wall 192. The curvature and orientation of the recess 188 is not arbitrary. In some embodiments, the radius of curvature for the bottom wall 196 and the top wall 194 may be between about 25 mm and about 55 mm. In some embodiments, the radius of curvature for the bottom wall 196 may be between about 30 mm and about 32 mm, for example about 31 mm. In some embodiments, the radius of curvature for the top wall 194 may be between about 46 mm and about 50 mm, for example about 48 mm. With respect to the radii of curvature noted above, when referring to the same geometric centerpoint, the radius of curvature from that centerpoint to the geometric center of the pin 184 may be between about 36 mm and about 44 mm, for example about 40 mm. In other embodiments, the recess 188 may be linearly straight between the front wall 190 and the rear wall 192. In some embodiments, the length 198 of the recess 188 may be angularly offset, relative to the upper sagittal axis 23, by up to about 20 degrees, up to about 15 degrees, up to about 10 degrees, or another suitable angle range. In some embodiments, the recess 188 may be angularly offset from the upper sagittal axis 23 by about 11 degrees. In some embodiments, the recess 188 may be angularly offset from the upper sagittal axis 23 by about 15 degrees. In other embodiments, the recess 188 may be substantially parallel to the upper sagittal axis 23 (i.e. be angularly offset from the sagittal axis 23 by zero degrees).

Figure 14B:
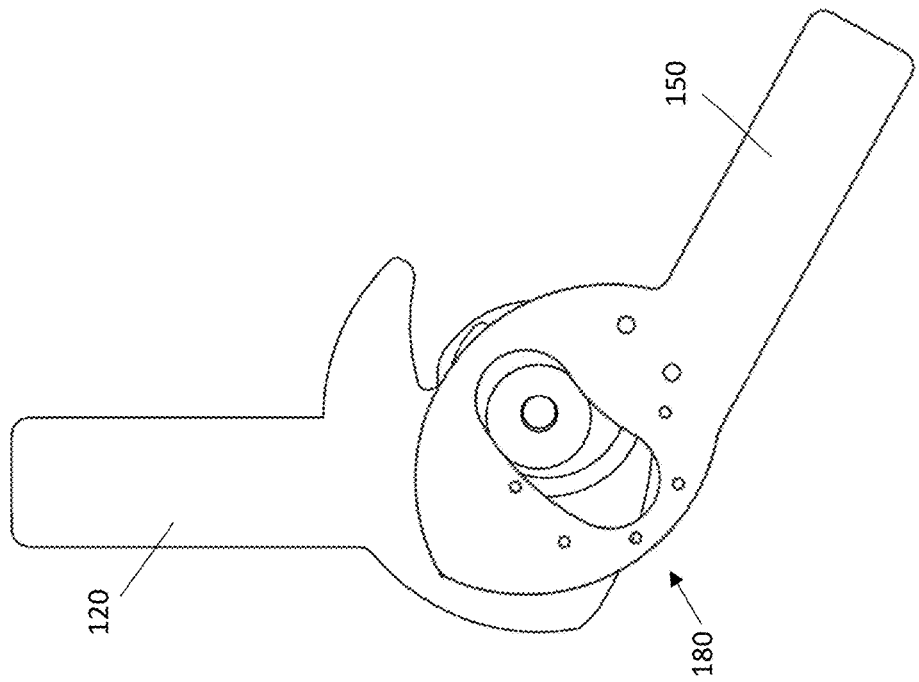
FIG. 14B depicts the support member of FIG. 14A in a second configuration.
Figure 14A:
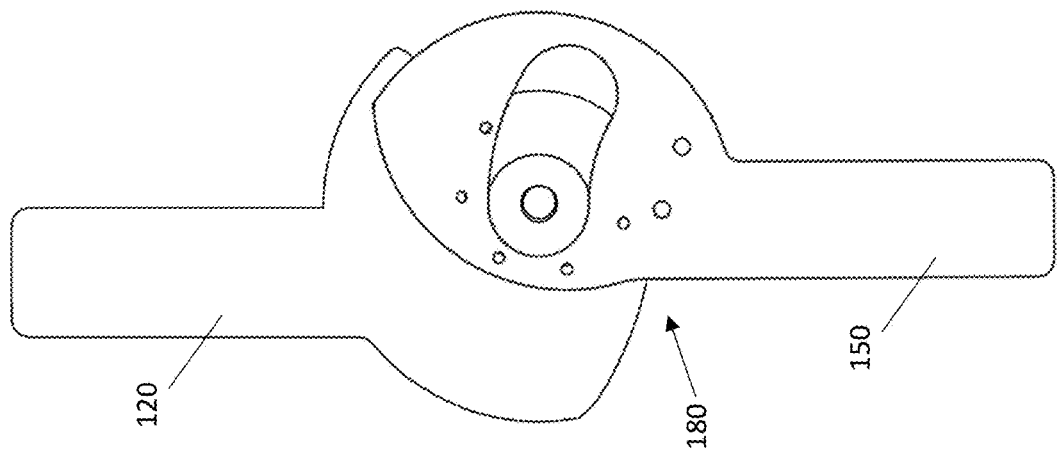
FIG. 14A depicts a support member in a first configuration according to an aspect of this disclosure.

The hinge 180 may include a first configuration and a second configuration. In the first configuration, the pin 184 is disposed in a first position within the recess 188, and in the second configuration, the pin 184 is disposed in a second position within the recess 188, where the second position is translationally spaced from the first position along the length 198 of the recess 188. The hinge 180 may be configured to be moved between the first and second configuration, for example, when the wearer flexes or extends the knee. In some aspects, the translational movement along the length 198 of the recess 188 may be parallel to the at least one of the upper and lower sagittal axes 23 and 33. Exemplary first and second configurations are depicted in FIGS. 14A and 14B, respectively. It will be understood that the hinge 180 may include a plurality of configurations other than the two depicted first and second configurations, and that the shown configurations are for comparison and exemplary purpose and are do not limit the range of rotation and/or translation of the first and second bodies 120 and 150 relative to each other. It should be further understood that movement between the pin 184 and the recess 188 is described in relative terms, some embodiments may include the pin 184 being movable relative to the recess 188, while other embodiments may include the recess 188 being movable relative to the pin 184. It should be appreciated that this disclosure is not limited to movement of only the pin 184 or only the recess 188, but rather for relative displacement between the pin 184 and the recess 188. A common drawback of existing knee braces is that the knee brace does not stay in position, but instead moves out of place relative to the wearer's leg and knee joint. This occurs because the brace cannot match the natural knee motion. The disclosed embodiments help to overcome this disadvantage.

As explained above, the lower leg 4 pivots relative to the upper leg 3 around the knee joint 5 (for example, pivots around the upper transverse axis 22). However, during the full range of flexion/extension, at least a portion of the lower leg 4 slides along the upper leg 3 and translates relative to the upper leg 3 (for example, along the upper sagittal axis 23). When the depicted knee brace 10 is affixed to the leg 2, the leg's rotational motion (about the upper transverse axis 22) is matched by the rotation of the pin 184 within the recess 188. The leg's translational motion (along the upper sagittal axis 23) is matched by the translation of the pin 184 within the recess 188 from the first position to the second position along the length 198 of the recess 188. By having a hinge 180 capable of both rotational and translational motions that match the natural rotational and translational motions of the leg as the leg moves between flexion and extension, the disclosed brace 10 can have a desired range of motion while being fixedly attached to the leg. By matching ranges of motion, the brace 10 does not apply undesired stresses on the knee joint due to an inability to follow the natural flexing or extending motion range of the leg. This decreases pain and risk of injury, while increasing comfort for the wearer and durability of the brace.

Figure 15:
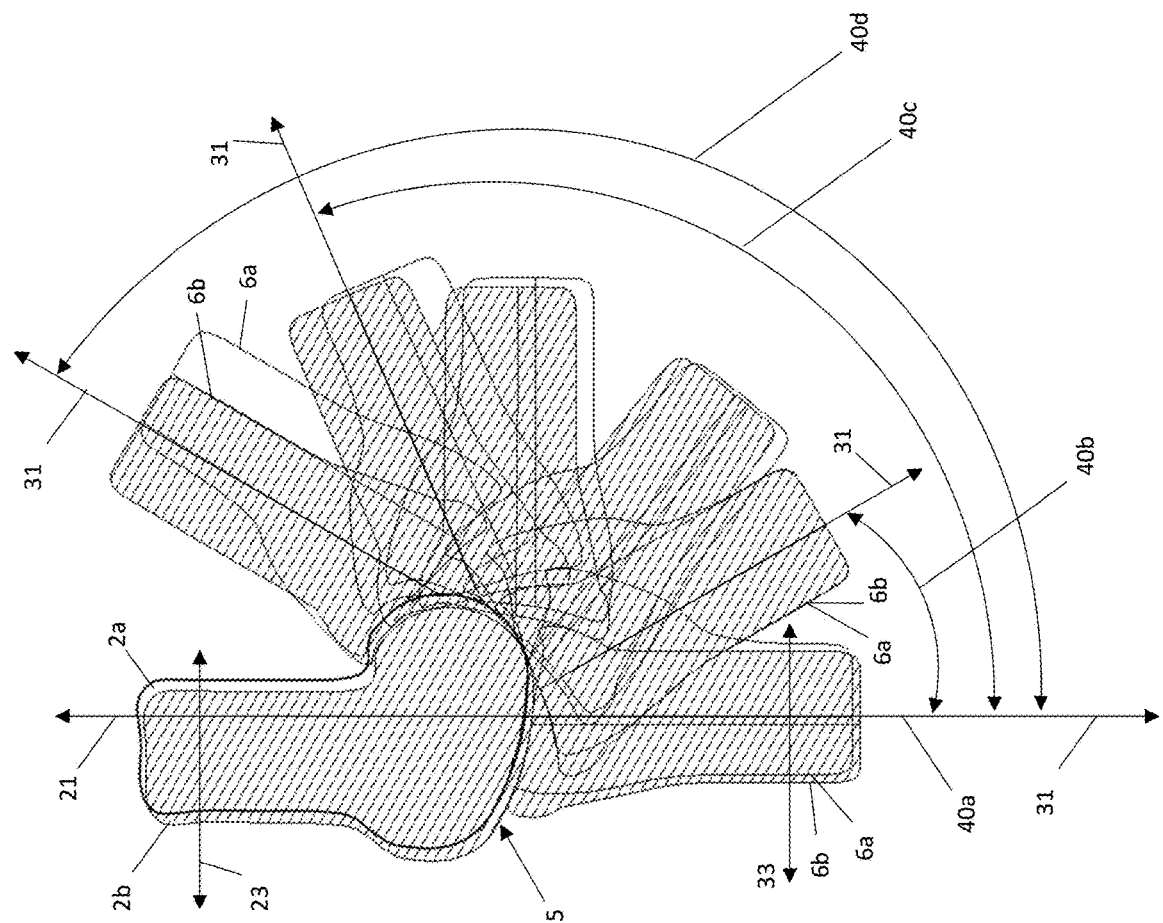
FIG. 15 depicts a flexion-extension path of a leg according to an aspect of the disclosure.

As the leg 2 moves between an extended configuration and a flexed configuration, the lower leg 4 not only pivots around the upper transverse axis 22 and translates along the upper sagittal axis 23, but the lower leg 4 also rotates around the lower frontal axis 31 relative to the upper frontal axis 21. This phenomenon is depicted in FIG. 15, which shows a flexion-extension pathway between full extension of the knee (i.e. when the lower leg 4 is at the maximum flexion angle 40 relative to the upper leg 3) and full flexion of the knee (i.e. when the lower leg 4 is at the minimum flexion angle 40 for the individual). FIG. 15 shows a cross-sectional view of the lateral side 2a of the leg 2 (not hashed) and a cross-sectional view of the medial side 2b of the same leg 2 (hashed) overlaid over the lateral side 2a. An exemplary range of motion between extension and flexion of the knee is depicted, showing various flexion angles 40 measured between the upper frontal axis 21 and the lower frontal axis 31. As shown in FIG. 15, when the leg is in the fully extended position, the upper and lower frontal axes 21 and 31 are not angularly offset from each other. This is depicted by a first flexion angle 40a, which corresponds to approximately zero degrees between the upper and lower frontal axes 21 and 31. As the knee is flexed, the relative flexion angle 40 increases. A second flexion angle 40b is depicted showing an angle of approximately 30 degrees between the lower frontal axis 31 and the upper frontal axis 21. A third flexion angle 40c is depicted showing an angle of approximately 120 degrees between the lower and upper frontal axes 31 and 21. A fourth flexion angle 40d is shown showing an angle of approximately 150 degrees between the lower and upper frontal axes 31 and 21. The four depicted flexion angles 40a, 40b, 40c, and 40d are exemplary and are used for descriptive purposes only. Typically, the range of motion for an average human between full extension of the knee and full flexion of the knee ranges from approximately zero degrees to approximately 150 degrees (i.e. from the first flexion angle 40a to the fourth flexion angle 40d). It will be understood that this range is exemplary and individual ranges of motion may vary.

As the leg 2 moves from extension to flexion, the lower leg 4 rotates around the lower frontal axis 31 relative to the upper leg 3. To schematically depict this relative rotation, an anterior point 6a of the lower leg 4 is shown in FIG. 15, being shown as a lateral anterior point 6a on the cross-section of the lateral side 2a of the leg 2 (not hashed) and as a medial anterior point 6b on the cross-section of the medial side 2b of the leg 2 (hashed). As can be seen from FIG. 15, when the lower leg 4 is at a first flexion angle 40a relative to the upper leg 3 (i.e. when the flexion angle 40 is approximately zero), the lateral anterior point 6a is translationally offset from the medial anterior point 6b along a first direction parallel to the lower sagittal axis 33. When the lower leg 4 is at a second flexion angle 40b relative to the upper leg 3 (i.e. when the flexion angle is approximately 30 degrees), the lateral and medial anterior points 6a and 6b overlap when viewed in the cross-section defined by the lower sagittal axis 33 and the lower frontal axis 31. When the lower leg 4 is at a third flexion angle greater than the second flexion angle 40b, (for example, when the flexion angle 40 is greater than approximately 30 degrees), the lateral anterior point 6a is translationally offset from the medial anterior point 6b along a second direction parallel to the lower sagittal axis 33 and opposite the first direction. Although the second flexion angle 40b is depicted as being approximately 30 degrees, it will be understood that human anatomy may differ between individuals, and the exact flexion angle at which the lateral and medial anterior points 6a and 6b overlap may include a different angle. It will be further understood that at angles lower than the second flexion angle 40b, the lateral anterior point 6a is offset from the medial anterior point 6b along the first direction parallel to the lower sagittal axis 33, while at flexion angles greater than the second flexion angle 40b, the lateral anterior point 6a is offset from the medial anterior point 6b along the second direction parallel to the lower sagittal axis 33 and opposite the first direction. For purposes of this disclosure, the second flexion angle 40b will be referred to as the angle along the flexion-extension range of motion where the lateral anterior point 6a and the medial anterior point 6b are not offset along the direction parallel to the lower sagittal axis 33.

An axial angle 42 between the lateral anterior point 6a and the medial anterior point 6b varies between full extension and full flexion of the leg 2. When the lower leg 4 is flexed and oriented relative to the upper leg 3 such that the lower leg 4 is at the second flexion angle 40b (for example, when the flexion angle 40 is approximately 30 degrees), the axial angle 42 is approximately zero. When the lower leg 4 is fully extended relative to the upper leg 3 such that the lower leg 4 is at the first flexion angle 40a (for example, when the flexion angle 40 is approximately zero degrees), the axial angle 42 is approximately 10 degrees (measured from a line parallel to the lower transverse axis 32). When the lower leg 4 is fully flexed relative to the upper leg 3 such that the lower leg 4 is at the fourth flexion angle 40d (for example, when the flexion angle 40 is approximately 150 degrees), the axial angle 42 is approximately negative 30 degrees. That is, as the leg 2 moves from full extension to full flexion (i.e. from a flexion angle 40 of approximately zero degrees to a flexion angle 40 of approximately 150 degrees), the lower leg 4 rotates around the lower frontal axis 31 for approximately 40 degrees.

It may be advantageous for the worn knee brace to follow the axial rotation of the lower leg 4 in addition to following the knee flexion and translation of the lower leg 4 relative to the upper leg 3 as described above. In practice, it may be beneficial to cause the lower leg 4, at the medial side 2b of the leg 2, to translate along the first direction farther than the lower leg 4 at the lateral side 2a, along the flexion path between the first flexion angle 40a and the second flexion angle 40b. Furthermore, it may be beneficial to cause the lower leg 4 at the lateral side 2a to translate along the first direction farther than the lower leg 4 at the medial side 2b along the flexion path between the third flexion angle 40c and the fourth flexion angle 40d. That is, along approximately the first 30 degrees from full extension to the first flexion angle 40a, the medial side 2b of the lower leg 4 can translate farther along the first direction relative to the lateral side 2a of the lower leg 4; and along approximately the last 30 degrees of full extension to the fourth flexion angle 40d, the lateral side 2a of the lower leg 4 can translate farther along the first direction relative to the medial side 2b of the lower leg 4.

Figure 16:
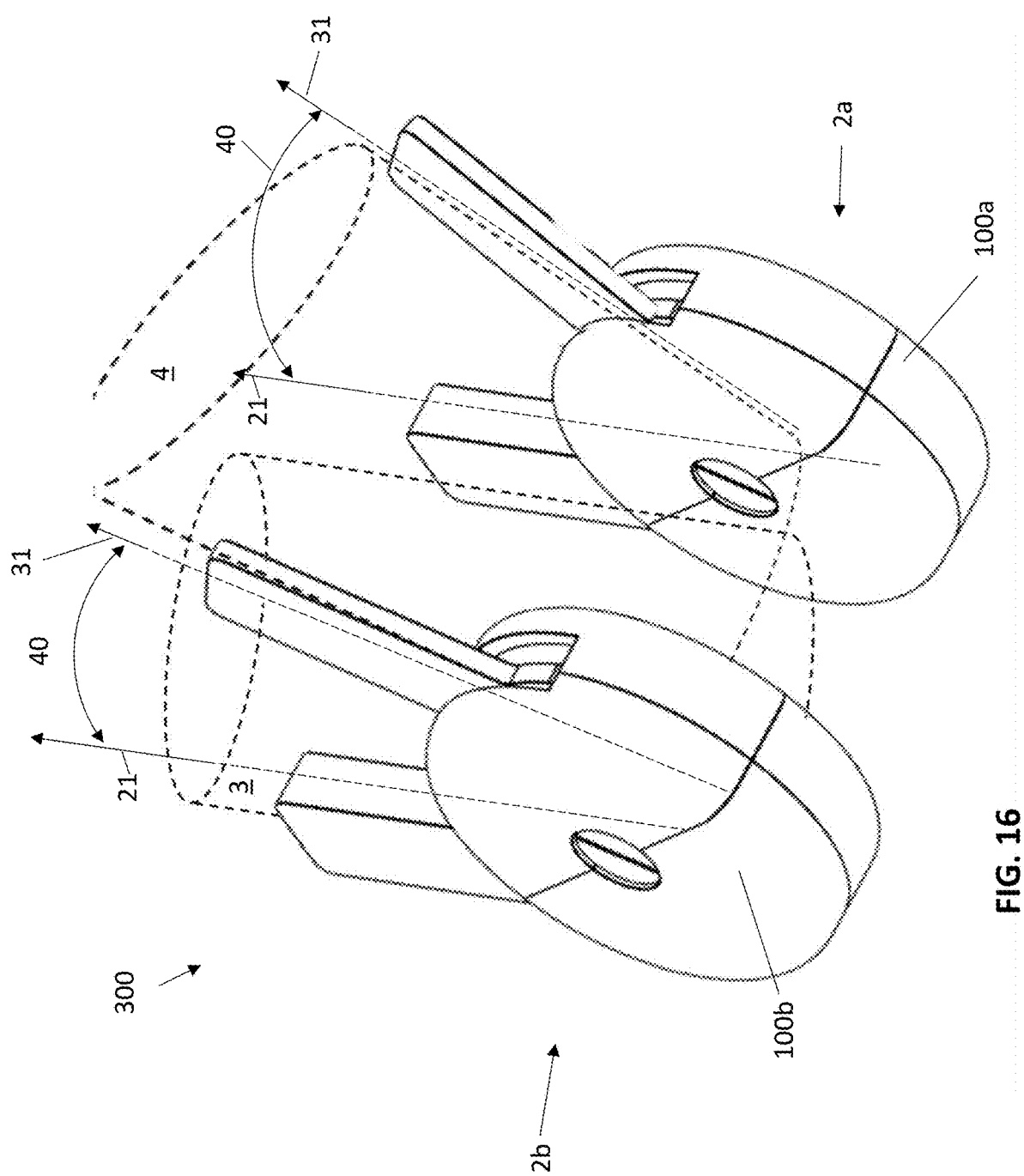
FIG. 16 depicts a knee brace according to yet another aspect of the disclosure.

In some embodiments, the knee brace 10 may be configured to account for the axial rotation of the lower leg 4 along the lower frontal axis 31 relative to the upper leg 3. The brace 10 may include two support modules 100, with one support module being disposed adjacent the lateral side 2a of the leg 2 and the other support module being disposed adjacent the medial side 2b of the leg 2. Each of the two support modules 100 may be configured to translate and rotate at different distances relative to teach other to coincide with the different relative rotations of the lateral and medial sides of the lower leg during flexion and extension as described above. Referring to FIG. 16, a lateral support module 100a is shown coupled contacting the lateral side 2a of the leg 2. A medial support module 100b is shown coupled contacting the medial side 2b of the leg 2. In order to account for the axial rotation of the lower leg 4 described above, the two support modules 100a and 100b may be configured to rotate along and around their respective hinges 180 independently of one another. That is, along the full flexion-extension motion path, the flexion angle 40 of the lateral support module 100a need not always be the same as the flexion angle 40 of the medial support module 100b. Referring to the description above regarding axial angles 42, in some embodiments, the flexion angle 40 of the lateral support module 100a may be smaller than the flexion angle 40 of the medial support module 100b (e.g. between the first flexion angle 40a and the second flexion angle 40b, as referenced in FIG. 15). In other cases, the flexion angle 40 of the lateral support module 100a may be larger than the flexion angle 40 of the medial support module 100b (e.g. between the third flexion angle 40c and the fourth flexion angle 40d, as referenced in FIG. 15). It will be understood that, due to the varying nature of human anatomy, the exact angles can differ between individuals.

In some embodiments, it may be advantageous to account for the axial rotation of the lower leg 4 at only some portions of the full flexion-extension pathway (for example, approximately the first 30 degrees and approximately the last 30 degrees). Disclosed embodiments of the brace 10 may have lateral and medial support modules 100a and 100b that are configured to rotate and translate around and along their respective hinges 180, relative to one another, for different distances and angles at some portions of the flexion-extension pathway, while rotating and translating for equal distances at other portions of the flexion-extension pathway. Referring again to FIGS. 15 and 16, for example, the medial support module 100b may be configured to rotate and translate along its hinge 180 for more degrees (measured as the flexion angle 40) and along a greater distance along the length 198 of the recess 188, relative to the rotation and translation of the lateral support module 100a, between the first flexion angle 40a and the second flexion angle 40b. Conversely, the lateral support module 100a may be configured to rotate and translate along its hinge 180 for more degrees and along a greater distance along the length 198 of the recess 188 relative to the rotation and translation of the medial support module 100b between the third flexion angle 40c and the fourth flexion angle 40d. For the portion of the flexion-extension path between the second flexion angle 40b and the third flexion angle 40c, the relative degree of rotation around pin 184 and translation along the length 198 of the recess 188 may be substantially the same for both the lateral and the medial support modules 100a and 100b.

Figure 17A:
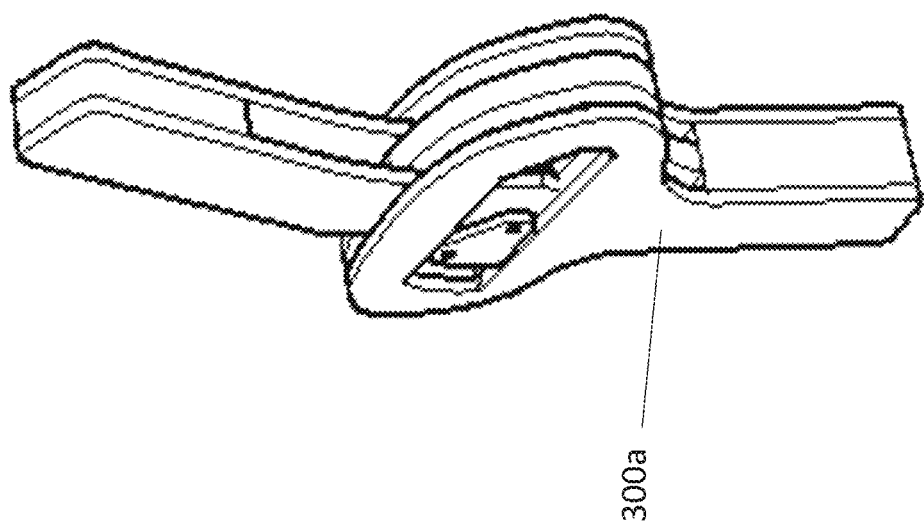
FIG. 17A depicts a lateral support member for a knee brace according to another aspect of the disclosure.
Figure 17B:
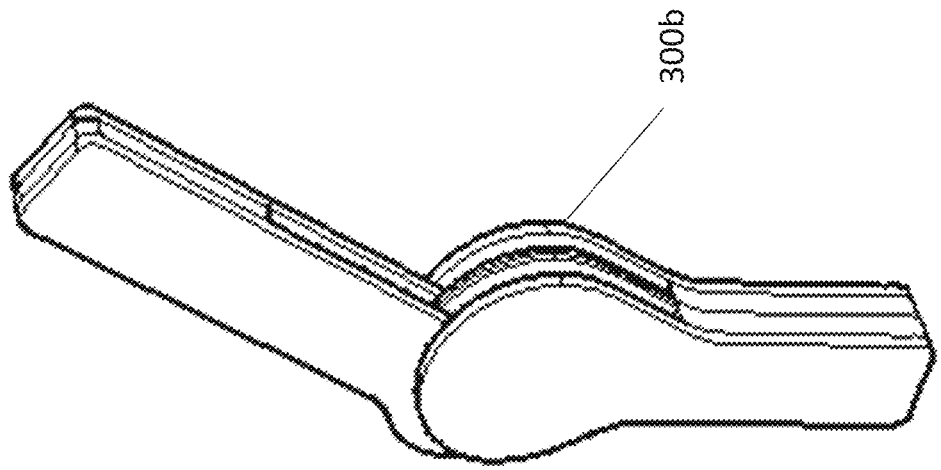
FIG. 17B depicts a medial support member for a knee brace according to another aspect of the disclosure.

According to some embodiments, the pin 184 and the recess 188 may define a geared configuration that can be adjusted based on individual anatomical parameters. The geared configuration may be configured to allow for different rates of rotation around the pin 184 and translation within the recess 188 at different portions of the flexion-extension pathway. Referring to FIGS. 17A and 17B, two support modules 300 are depicted (FIG. 17A shows a lateral support module 300a, and FIG. 17B shows a medial support module 300b). Unless noted otherwise, components of support modules 300 may be substantially the same as those of support modules 100 described above. In some embodiments, during flexion and extension, the medial support module 300b may be configured to translate along the hinge 180 along the length 198 of the recess 188 at a constant rate. That is, the second body 150 is configured to translate within the recess 188 for a fixed distance along the length 198 per unit of rotation around the pin 184. In some exemplary embodiments, the medial support module 300b may be configured such that the pin 184 translates within the recess 188 for approximately 2.6 mm for every 30 degrees of rotation of the pin 184 within the recess 188. This may be constant for the entire flexion-extension pathway, such that the translation-to-rotation rate is the same between the first flexion angle 40a (i.e. full extension) to the fourth flexion angle 40d (i.e. full flexion).

The lateral support module 300a may be configured to move in a corresponding pattern. However, in some embodiments, the lateral support module 300a may be configured to follow a different translation path. For example, the rate of translation relative to rotation of the lateral support module 300a may vary along the flexion-extension pathway. In some embodiments, the lateral support module 300a may be configured such that the pin 184 translates within the recess 188 for approximately 2.6 mm for every 30 degrees of rotation of the pin 184 within the recess 188, but only for a portion of the flexion-extension pathway shown in FIG. 15. In some exemplary embodiments, the lateral support modules 300a may have a translation-to-rotation rate of approximately 9.5 mm translation for every 30 degrees of rotation between the first flexion angle 40a and the second flexion angle 40b; approximately 2.6 mm translation for every 30 degrees of rotation between the second flexion angle 40b and the third flexion angle 40c; and approximately 24.6 mm translation for every 30 degrees of rotation between the third flexion angle 40c and the fourth flexion angle 40d.

Figure 18:
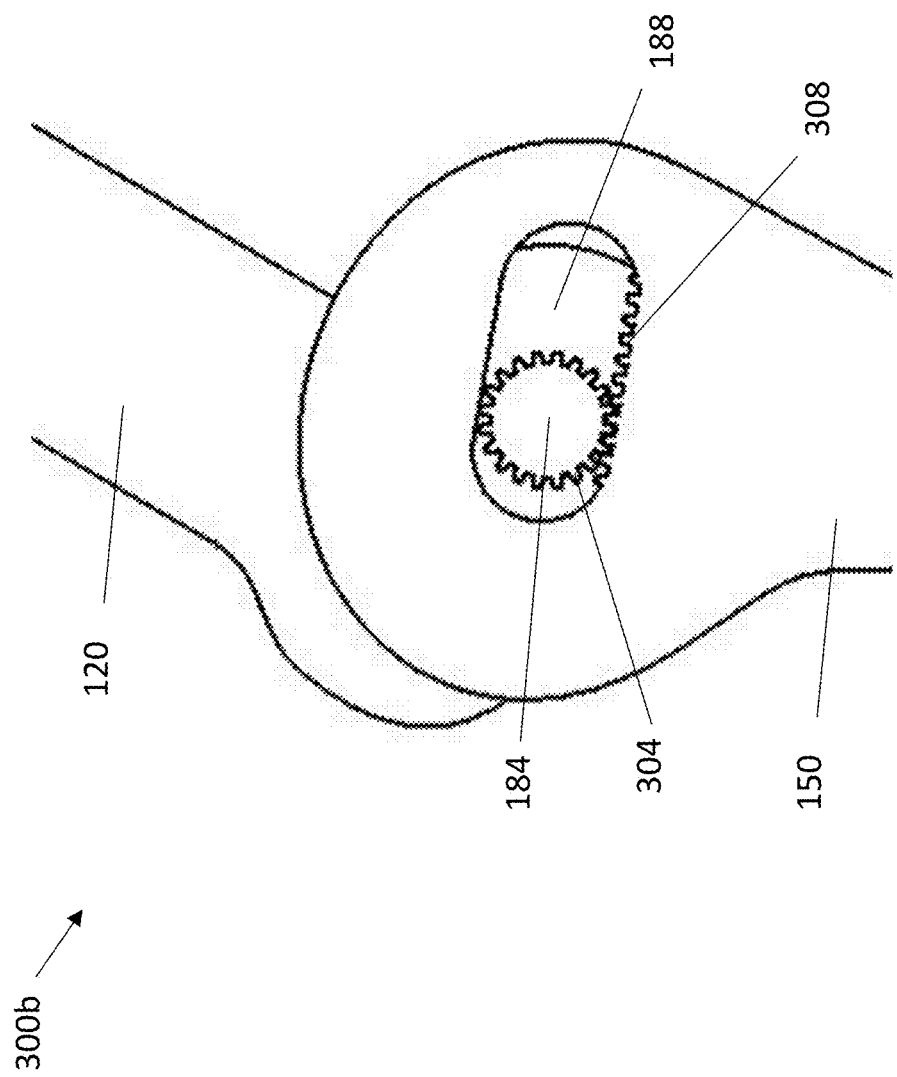
FIG. 18 depicts a side perspective view of a portion of the medial support member of FIG. 17B.
Figure 19B:
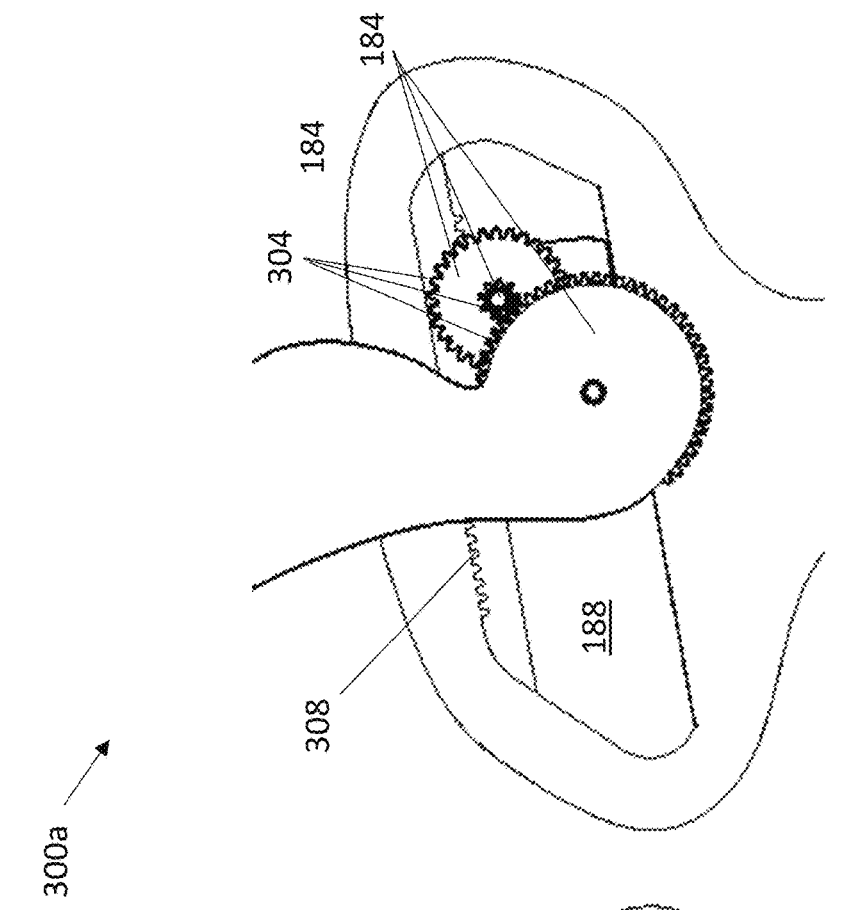
FIG. 19B depicts another side perspective view of the portion of the lateral support member of FIG. 17A.
Figure 19A:
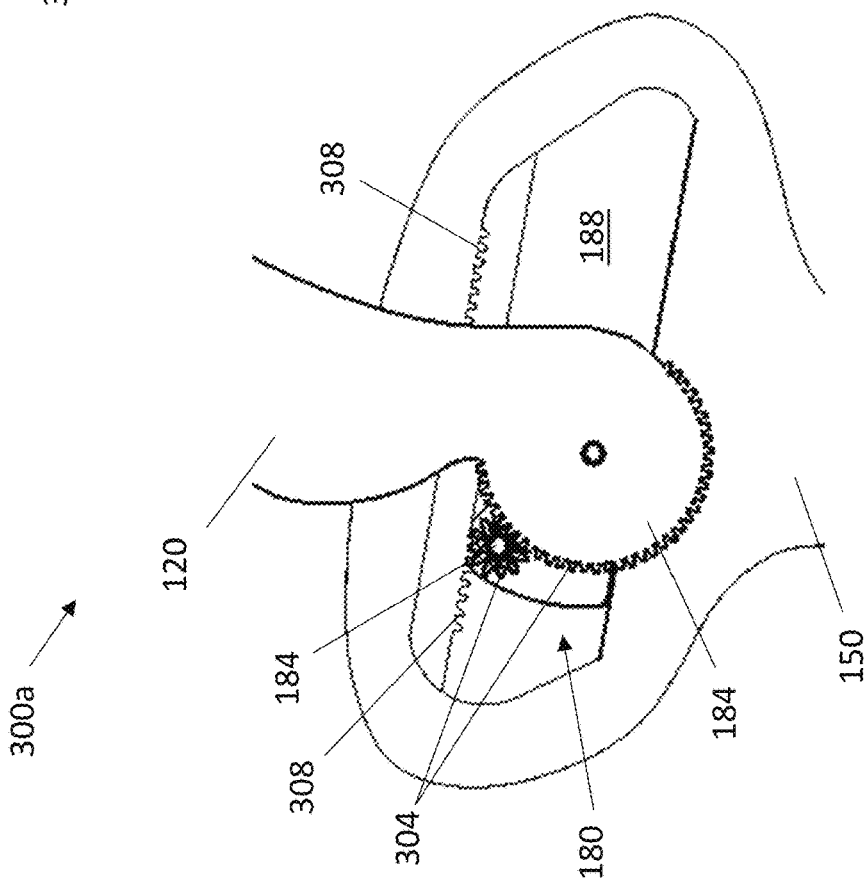
FIG. 19A depicts a side perspective view of a portion of the lateral support member of FIG. 17A.

The variation of translation-to-rotation rate described above may be accomplished by the use of complex gears that can make up the hinge 180. Referring to FIGS. 18, 19A, and 19B, exemplary hinges 180 are depicted, showing various pinions in connection with respective racks. FIG. 18 depicts a medial support module 300b according to an embodiment. FIG. 18 shows a pin 184 within a recess 188. The pin 184 defines teeth 304 disposed circumferentially around the pin 184. The recess 188 can include a rack of teeth 308 configured to operatively receive the teeth 304 from the pin 184 as the pin 184 translates within the recess 188 along its length 198. The teeth 308 may be disposed on the bottom wall 196 of the recess 188. Alternatively, or additionally, the teeth 308 may be disposed on the top wall 194.

Figure 19C:
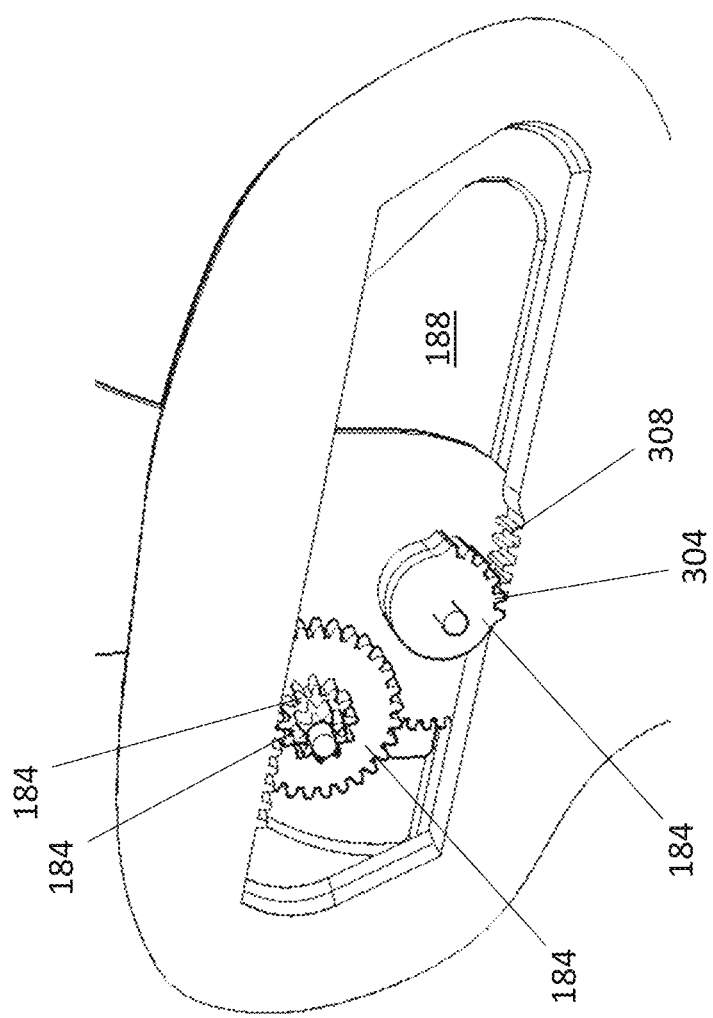
FIG. 19C depicts a cross-sectional perspective view of the portion of the lateral support member of FIG. 19A.

Referring to FIGS. 19A-19C, a lateral support module 300a is shown according to an embodiment. FIG. 19A shows the lateral support module 300a viewed from the lateral side 2a, and FIG. 19B shows the lateral support module 300a viewed from the medial side 2b. A plurality of pinions and respective racks can make up the hinge 180 on the lateral support module 300a. So, some embodiments may include a plurality of pins 184 that are coupled with each other and define teeth 304 thereon that are configured to engage with respective teeth 308 disposed on portions of the recess 188. The combination of different pins 184 can make up a series of complex gears that can be used to arrive at the desired translation of the pins 184 with in the recess 188 based on the rotation of the second body 150 relative to the first body 120. FIG. 19C shows another cross sectional view of the lateral support module 300a shown in FIG. 19A, showing internal gearing mechanisms. As shown in FIG. 19C, one or more of the plurality of pins 184 may be a slip gear, where a portion, but not the entirety, of the circumference of the pin 184 includes teeth 304 extending therethrough. The plurality of pins 184 are configured to precisely control the translation of the first body 120 relative to the second body 150 within the recess 188. Individual pins 184 may contact at least one other pin 184 to transfer rotational motion relatively between the first body 120 and the second body 150.

In some exemplary experimental embodiments, an embodiment of the knee brace 10 may include support struts 200 that are different shapes and/or dimensions between the lateral support module 100a and the medial support module 100*b*. By having the support struts 200 differ based on which side of the leg 2 the support module 100 is on (i.e. at the lateral side 2*a* or the medial side 2*b*), the brace can help translate the three-dimensional aspects of the knee joint into two two-dimensional components. In some embodiments, the support struts 200 on the lateral support module 100*a* may be approximately 40 mm in length. In some embodiments, the support struts 200 on the medial support module 100*b* may be approximately 60 mm in length. An average, healthy human knee has a posteriorly declined slope of the medial tibial plateau of approximately 10 degrees. As such, embodiments of medial support modules 100*b* may have a corresponding slope of approximately 11 degrees, and lateral support modules 100*a* may have a corresponding slope of approximately 15 degrees. The lateral tibial plateau epicenter is slightly superior and posterior to the medial tibial plateau in the average, healthy human leg.

In some embodiments, the brace 10 may be configured to resist hyperextension of the wearer's knee joint 5 (i.e. rotation of the lower leg 4 relative to the upper leg 3 such that the flexion angle is less than the first flexion angle 40*a*). Each support module 100 may be configured to allow relative rotation and translation between the first body 120 and the second body 150 for a range of flexion-extension motion defined between the first flexion angle 40*a* and the fourth flexion angle 40*d*, but not beyond either the first or the fourth flexion angles 40*a* and 40*d*. This prevents accidental hyperextension or hyperflexion of the knee, which can lead to damage to the knee joint. The limiting of the range of motion can be accomplished by the connection of the support struts 200 between the first body 120 and the second body 150. The support struts 200 are not deformable, and as such can serve as physical tensile stops to prevent relative rotation between the first and second bodies 120 and 150 beyond a predetermined range. In some embodiments, a stopping surface 130*a* may be disposed on one of the first and second bodies 120 and 150 and be configured to contact a corresponding stopping surface 130*b* disposed on the other of the first and second bodies 120 and 150 (see FIGS. 8-11). When the first body 120 rotates relative to the second body 150 in a rotational direction and the stopping surfaces 130*a* and 130*b* contact each other, further rotation in the same rotational direction is prevented. Additional stopping surfaces, for example surfaces 130*c* and 130*d*, which are configured to contact one another and inhibit rotation in the opposite rotational direction.

Figure 20C:
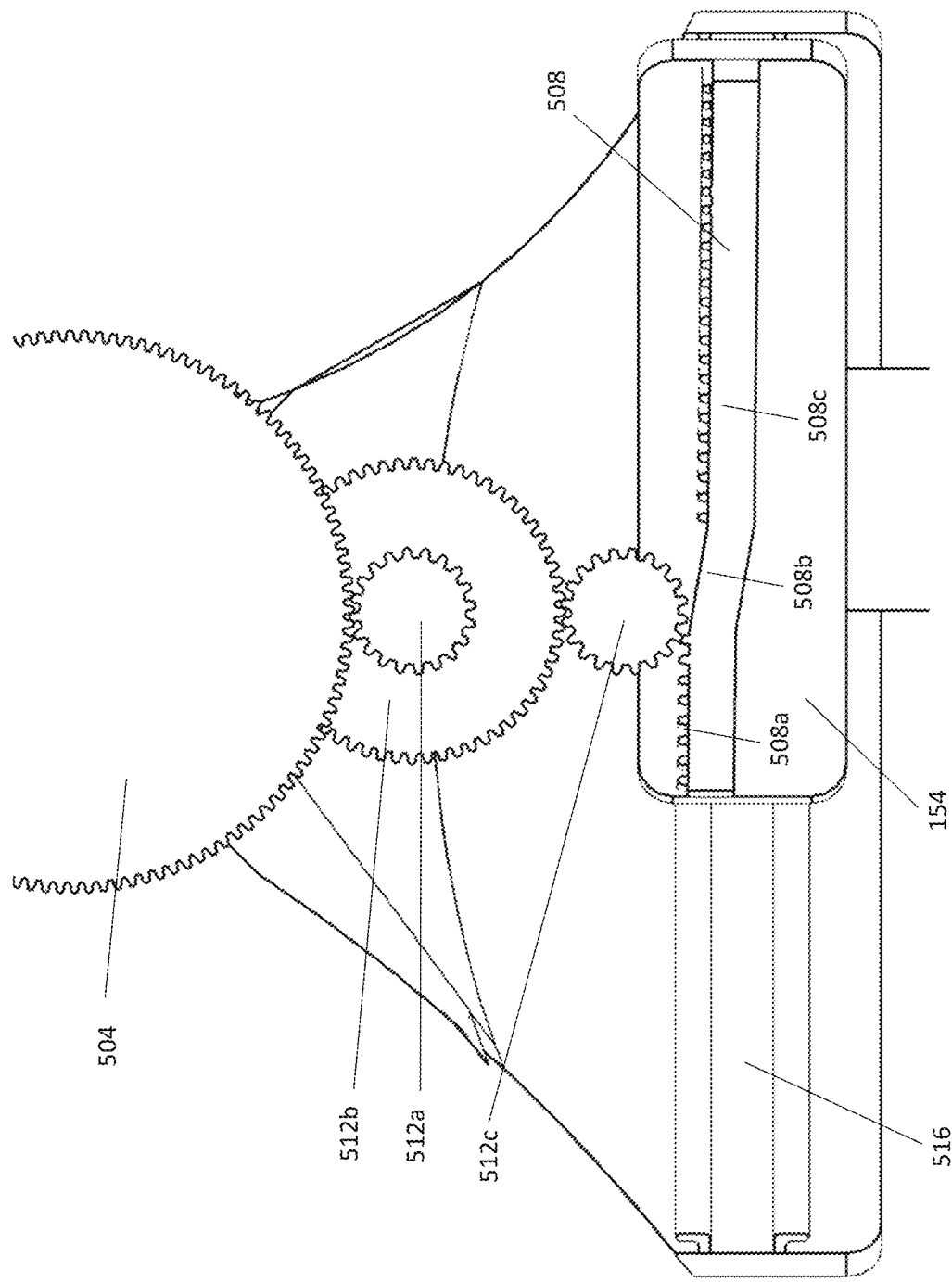
FIG. 20C depicts a side perspective view of a portion of the support member of FIG. 20A.

Referring to FIGS. 20A-22E, alternative embodiments of knee braces are disclosed. Components shown in FIGS. 20A-22E can be similar or the same as like-referenced components described throughout this specification unless noted otherwise. Referring to FIGS. 20A-20C, portions of a knee brace embodiment are shown. The figures specifically show a support module 500 configured to be utilized within a knee brace 10 on the lateral side 2*a* of the leg 2. In some embodiments, the support module used for the medial side 2*b* of the leg 2 in such braces can be one of the disclosed support modules 100 or 300*b* described above. The support module 500 includes a first body 120 rotationally and translationally coupled to a second body 150 at a hinge 180. The hinge 180 may include one or more gear assemblies. The hinge 180 may include a pin 184 within a recess 188, as described throughout this application. The pin 184 may be a pinion and may include teeth 304 disposed circumferentially around the pin 184 and configured to engage with complementary teeth 308 disposed within the recess 188, such as described, for example, in reference to FIG. 18 above (the pin 184 with teeth 304 can be referred to as a pinion, and the teeth 308 on the recess 188 may be referred to as a rack for the pinion).

As shown in FIGS. 20A-20C, the first body 120 may include a first pinion 504, for example on the head 124 of the first body 120. The second body 150 may include a rack 508 configured to engage, either directly or indirectly, with the first pinion 504. The rack 508 may be disposed on the head 154 of the second body 150. The hinge 180 may include a connecting hinge body 502 extending between the first body 120 and the second body 150 and being configured to movably be engaged with the first body 120 and the second body 150. The hinge body 502 may be pivotally connected to the first body 120, such that the first body 120 is configured to rotate and translate relative to the hinge body 502, similarly to how the first body 120 is described as translating and rotating relative to the rest of the support module 100 as described throughout this application. The hinge body 502 further defines a channel 516 therein. The second body 150 may be configured to be slidably movable within the channel 516. During flexion or extension of the knee brace 10, the first body 120 rotates and translates relative to the hinge body 502, and the second body 150 slidably translates within the channel 516. The translation of the second body 150 within the channel 516 is dictated by the rotation and translation of the first body 120 and by the interaction of the first pinion 504 with the rack 508. As shown in FIGS. 20A-20C, a plurality of intermediary pinions 512 may be disposed between the first pinion 504 and the rack 508. It will be understood that each of the intermediary pinions 512 are configured to engage with at least one other pinion, such that rotation of the first pinion 504 causes rotation of each of the intermediary pinions 512 and causes movement of the rack 508. The intermediary pinions 512 may be floating, such that they are not rigidly fixed to the hinge body 502. In some embodiments, one or more of the intermediary pinions 512 may be fixed to the first body 120, to the second body 150, or some fixed to the first body 120 and others fixed to the second body 150. Such an arrangement allows for relative translation of the first body 120 to the second body 150 without causing the intermediary pins 512 to disconnect from each other, from the first pinion 504, or from the rack 508. When the first pinion 504 is rotated, the intermediary pinions 512 also rotate accordingly, and the rack 508, which is fixedly coupled to the second body 150, is moved, causing the second body 150 to slidably translate within the channel 516. Referring to FIG. 20C, the support module 500 may include a first intermediary pinion 512*a* that is operatively coupled with the first pinion 504. A second intermediary pinion 512*b* is operatively coupled with the first intermediary pinion 512*a*, and is spaced away from the first pinion 504. A third intermediary pinion 512*c* is operatively coupled with the second intermediary pinion 512*b*. The third intermediary pinion 512*c* is also operatively coupled with the rack 508. As such, when the first pinion 504 is rotated, this rotation is passed onto the first intermediary pinion 512*a*, which in turn causes rotation of the connected second intermediary pinion 512*b*, which in turn causes rotation of the connected third intermediary pinion 512*c*, which in turn causes movement of the rack 508. It will be appreciated that the specific sizes of the pinions determines the relative rate of rotation of each pinion and the translation of the rack 508 relative to the rotation of the first pinion 504, and that the size and number of intermediary pinions 512 can be varied to arrive at the desired rate of translation of the second body 150 within the channel 516 per rate of rotation of the first body 120. The compound gear arrangements can reverse the rotational direction of the first pinion 504 multiple times. The first intermediary pinion 512a is engaged with the first pinion 504, and when the first pinion 504 rotates in a first rotational direction, the engaged first intermediary pinion 512a rotates in a second rotational direction opposite the first rotational direction (i.e. in a reversed direction). The second intermediary pinion 512b, which is fixedly coupled to the first intermediary pinion 512a, has a larger diameter than the first intermediary pinion 512a, which amplifies the effect of the rotation of the first intermediary pinion 512a. The second intermediary pinion 512b rotates in the same direction as the first intermediary pinion 512a. Rotation of the second intermediary pinion 512b in the second rotational direction causes rotation of the coupled third intermediary pinion 512c in the first direction, effectively reversing the rotational direction again to the original, first rotational direction. The third intermediary pinion 512c rides along the rack 508 and causes movement of the lower body 150. The rack 508 follows the shape of the channel 516. In some embodiments, the channel 516 is arcuate, semi-circular, or otherwise curved when viewed in the plane defined by the lower transverse and sagittal axes 32 and 33. As seen in FIG. 20C, the rack 508 may be discontinuous, such that the third intermediary pinion 512c is configured to engage with the rack 508 at a first portion (shown as 508a), disengaged from the rack 508 at a second portion (shown as 508b), and engage again with the rack 508 at a third portion (shown as 508c). When engaged with the third intermediary pinion 512c is engaged with the rack 508 (at either the first portion 508a or the third portion 508c), the lower body 150 orbits around a medial support member of the brace 10 (e.g. 100b or 300b). During flexion and extension of the brace 10, when the third intermediary pinion 512c is engaged with the first or third portions 508a or 508c of the rack 508, the lower body 150 is configured to axially rotate around the lower frontal axis 31. During flexion and extension of the brace 10, when the third intermediary pinion 512c is disengaged with the rack 508 (i.e. in the second portion 508b of the rack 508), the lower body 150 is not axially rotating around the lower frontal axis 31. That is, there is translation and rotation at the two extremes of flexion and extension, and just translation without any rotation in the mid-portion of sagittal motion.

As shown in FIG. 20C, the rack 508 may have an incline between the first portion 508a and the third portion 508c. The first and third portions 508a and 508c may be substantially parallel to each other as viewed in FIG. 20C, while the second portion 508b may be angularly offset and not parallel to the first and second portions 508a and 508c. In some embodiments, the incline of the second portion 508b may be approximately 10 degrees between the first portion 508a and the third portion 508c. In other embodiments, for example where the recess 188 is linearly flat and not arcuate, the first, second, and third portions 508a, 508b, and 508c may all be coplanar to each other, and there may be no incline relative to any of the three portions 508a-508c.

Figure 21C:
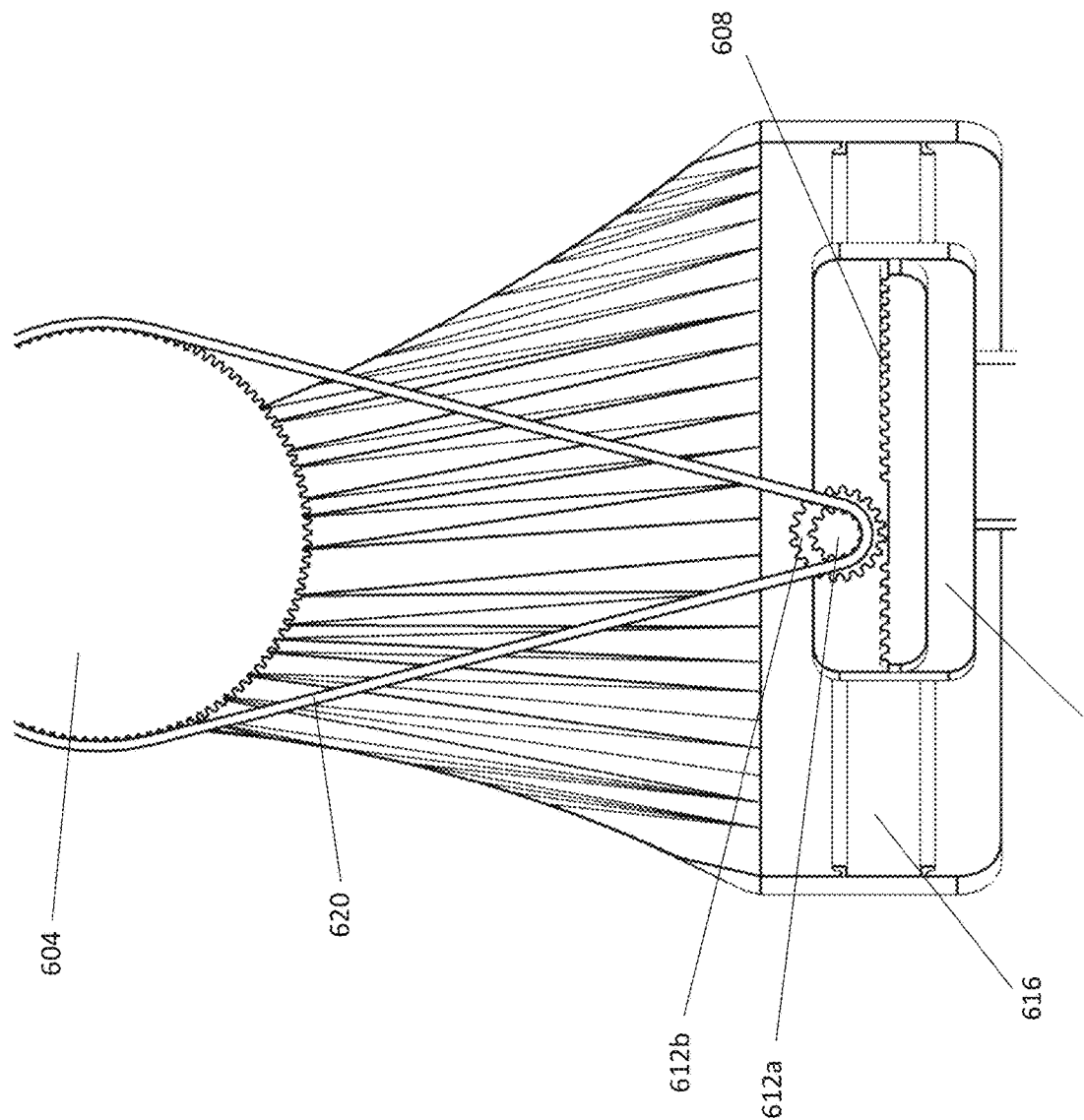
FIG. 21C depicts a side perspective view of a portion of the support member of FIG. 21A.

Referring to another embodiment of a support module 600 depicted in FIGS. 21A-21C, a different geared engagement between the first body 120 and the second body 150 is depicted. It will be understood that some of the components described with respect to the support module 600 may be similar or the same as those described with respect to the support module 500 and/or with respect to any of the support modules 100, 300a, or 300b described throughout this application. The support module 600 is configured to operate similarly to the support module 500, in that rotation and translation of the first body 120 along and around the hinge 180 causes translation of the lower body 150 relative to the hinge 180.

The first body 120 includes a first pinion 604 on the head 124 of the first body 120, which is configured to engage, either directly or indirectly, with a rack 608 defined on the second body 150, for example on the head 154 of the second body 150. The hinge 180 may include a connecting hinge body 602 extending between the first body 120 and the second body 150 and being configured to movably be engaged with the first body 120 and the second body 150. The hinge body 602 may be substantially the same as the hinge body 502 described above, except where noted below. A channel 616 is defined on the hinge body 602 and is configured to slidably receive the second body 150 therein. A plurality of intermediary pinions 612 may be disposed between the first pinion 604 and the rack 608. A belt 620 extends from the first pinion 604 to one of the intermediary pinions 612. As the first pinion 604 rotates, the belt 620 also rotates and causes rotation of the intermediary pinion 612 to which it is connected. Referring to FIG. 21C, the belt 620 is a closed loop and may contact the first pinion 604 around a portion of the circumference of the first pinion 604. The belt 620 also contact a first intermediary pinion 612a, such that when the first pinion 604 is rotated, the belt 620 is also rotated and causes the first intermediary pinion 612a to also rotate. The first intermediary pinion 612a is connected to a second intermediary pinion 612b, which is operatively engaged with the rack 608. As such, when the first pinion 604 is rotated, the belt 620 is moved along and relative to the circumference of the first pinion 604, and the translation of the belt 620 causes rotation of the operatively coupled first intermediary pinion 612a, which in turn causes rotation of the connected second intermediary pinion 612b, which in turn causes translation of the operatively engaged rack 608 within the channel 616.

The support module 600 may have a center of axial rotation, for example around the upper frontal axis 21 and/or the lower frontal axis 31, within the confines of the hinge 180. In an average human knee, natural rotation occurs around the medial condyle (generally around the upper frontal axis 21 and/or the lower frontal axis 31), and not around the medial knee skin. The average medial-lateral dimension of the average knee is approximately 80 mm, and the average anterior-posterior dimension is approximately 97 mm. On average, 10 degrees of rotation equates to approximately 6.9 mm of anterior-posterior translational motion, and 30 degrees equates to approximately 22.9 mm of anterior-posterior translational motion. The approximate average distance between the medial and lateral condyle centers is approximately 27 mm. This central rotation point in the center of the knee is approximately one-third (e.g. 27 mm divided by 80 mm) the distance from the medial skin surface, and approximately two-thirds the distance from the lateral side skin surface. This asymmetric location can need twice as much motion on the lateral side as the medial side. The radius of curvature for the lateral orbiting plate is then 53 mm rather than 80 mm, which has the effect of making the orbiting plate smaller.

The embodiment of the support module 600 is based on having both the medial and lateral portions of the brace 10 rotate in opposite directions around the knee's normal rotation point within the joint space itself. Because the rotation point of the brace 10 is much closer, the radius of curvature of the orbiting plate is smaller and the arc is tighter. This allows for a smaller footprint (i.e. narrower) than some other embodiments. Furthermore, the belt 620 can be used to connect the first pinion 604 directly to a first intermediary pinion 612a, which is fixedly coupled to the second intermediary pinion 612b, which can engage with the rack 508. This arrangement does not reverse rotational directions The first intermediary pinion 612a has a smaller diameter than the first pinion 604, which amplifies the effect of the larger first pinion 604. Such an arrangement may advantageously allow greater flexibility for the length and dimensions of the rack 608. Furthermore, the rack 608 of the support module 600 may be linear and be devoid of the incline described above with respect to the rack 508 in the support module 500, which can be advantageously easier to manufacture and assemble. In some embodiments of the support module 600, the medial orbiting plate may have a radius of curvature of approximately 27 mm, which makes its construction approximately one half the size of the lateral side. The medial support module (e.g. 100b or 300b) can then be constructed to move proportionally (e.g. approximately 50%) but in the opposite direction as the lateral support module 600. The reversal of motion is constructed by either adding or removing a gear in the appropriate location (described in detail below). The translational distance of the medial support module is then 50% of the lateral support module 600 for each 30 degrees of sagittal rotation. The rotational distance traveled during the axial rotation around the lower frontal axis 31 along the shorter radius arc is also approximately 50% less, but the angle subtended is still approximately 10 degrees and approximately 30 degrees respectively.

Referring to another embodiment of a support module 700 depicted in FIGS. 22A-22E, a different geared engagement between the first body 120 and the second body 150 is depicted. The support module 700 may be a medial support module that comprises a brace 10 having a lateral support module 600 as described above. It will be understood that some of the components described with respect to the support module 700 may be similar or the same as those described with respect to the support module 500 and 600 and/or with respect to any of the support modules 100, 300a, or 300b described throughout this application. The support module 700 is configured to operate similarly to the support modules 500 and 600, in that rotation and translation of the first body 120 along and around the hinge 180 causes translation of the lower body 150 relative to the hinge 180. Specifically, the support module 700 is configured to operate similarly, but in the opposite rotational direction, to the support module 600.

The first body 120 includes a first pinion 704 on the head 124 of the first body 120, which is configured to engage, either directly or indirectly, with a rack 708 defined on the second body 150, for example on the head 154 of the second body 150. The hinge 180 may include a connecting hinge body 702 extending between the first body 120 and the second body 150 and being configured to movably be engaged with the first body 120 and the second body 150. The hinge body 702 may be substantially the same as the hinge body 502 and/or the hinge body 602 described above, except where noted below. A channel 716 is defined on the hinge body 702 and is configured to slidably receive the second body 150 therein. A plurality of intermediary pinions 712 may be disposed between the first pinion 704 and the rack 708. A belt 720 extends between at least two intermediary pinions 712. The belt 720 may be substantially the same as the belt 620 described above. In the support module 700, the belt 720 may be operatively connected to two intermediary pinions 712 (instead of to one intermediary pinion 612 and the first pinion 604 as described in the embodiment for the support module 600). As shown in detail in FIGS. 22D and 22E, the first pinion 704 is operatively engaged with a first intermediary pinion 712a. The first intermediary pinion 712a is coupled with a second intermediary pinion 712b. The belt 720 circumferentially engages the second intermediary pinion 712b and a third intermediary pinion 712c spaced from the second intermediary pinion 712b. The third intermediary pinion 712c is coupled with a fourth intermediary pinion 712d (see FIG. 22E), which is operatively engaged with the rack 708. When the first pinion 704 rotates, the first intermediary pinion 712a also rotates, which causes the second intermediary pinion 712b, coupled to the first intermediary pinion 712a, to also rotate. Rotation of the second intermediary pinion 712b causes movement of the belt 720, which causes rotation of the third intermediary pinion 712c, which in turn causes rotation of the coupled fourth intermediary pinion 712d to rotate, which causes movement of the rack 708 relative to the fourth intermediary pinion 712d. The support module 700 may include one more intermediary pinion 712 than the number of intermediary pinions 612 in the support module 600. The addition of an extra intermediary pinion 712 causes reversal of the rotational direction relative to the rotational direction of the support module 600. In embodiments of the brace 10 where the support module 600 is the lateral support module 600 and the support module 700 is the medial support module 700 spaced opposite the lateral support module 600 and separated by the leg 2, it is necessary to have to rotational direction be in opposite direction between the two support modules 600 and 700 such that the brace 10 as a whole can flex and extend properly. It will be appreciated that the exact number of intermediary pinions 712 that is different from the number of intermediary pinions 612 does not have to be one; any odd number of intermediary pinions 712 may be added to the number of intermediary pinions 612 to achieve the desired reversal of rotational direction.

Figure 22C:
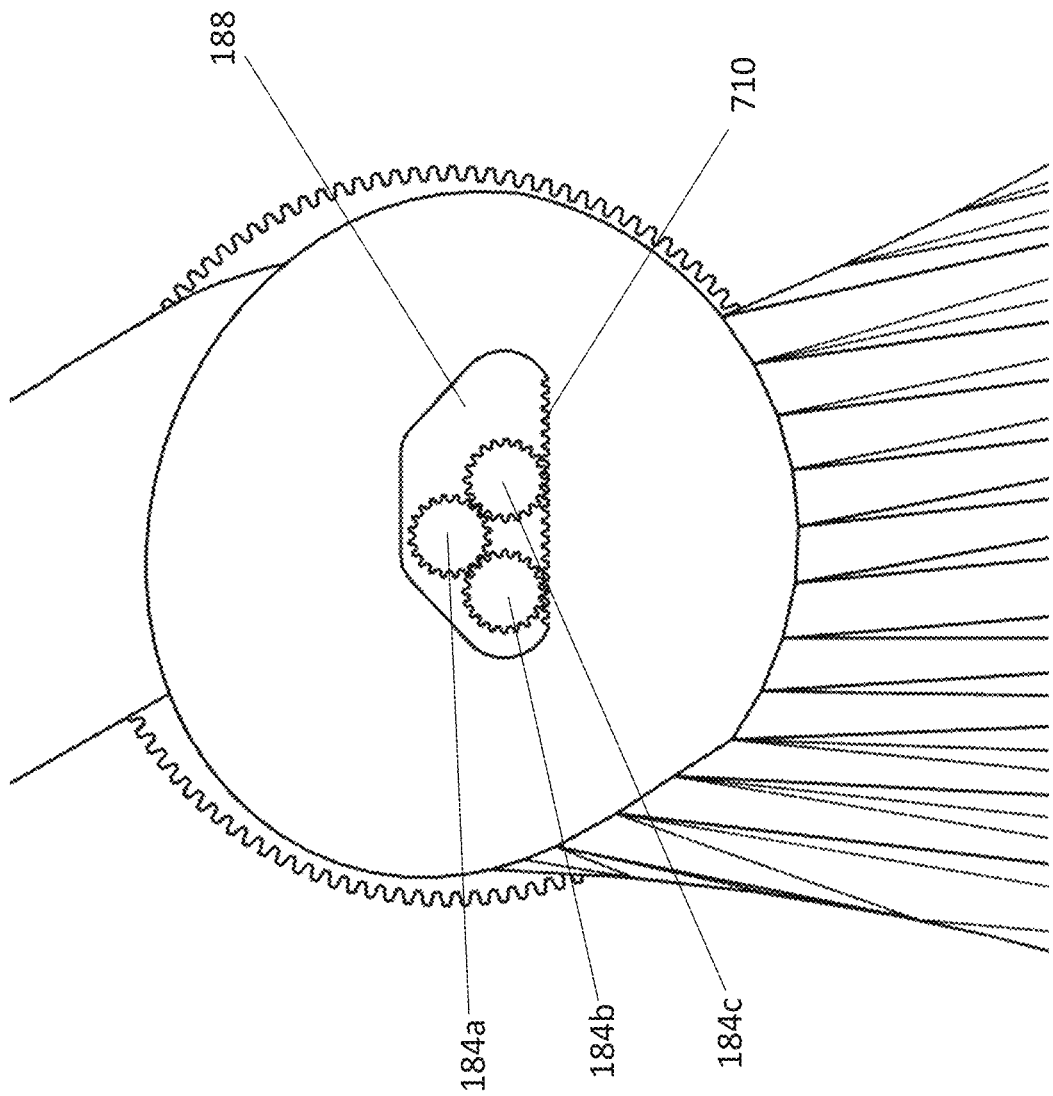
FIG. 22C depicts a side perspective view of a portion of the support member of FIG. 22A.
Figure 22D:
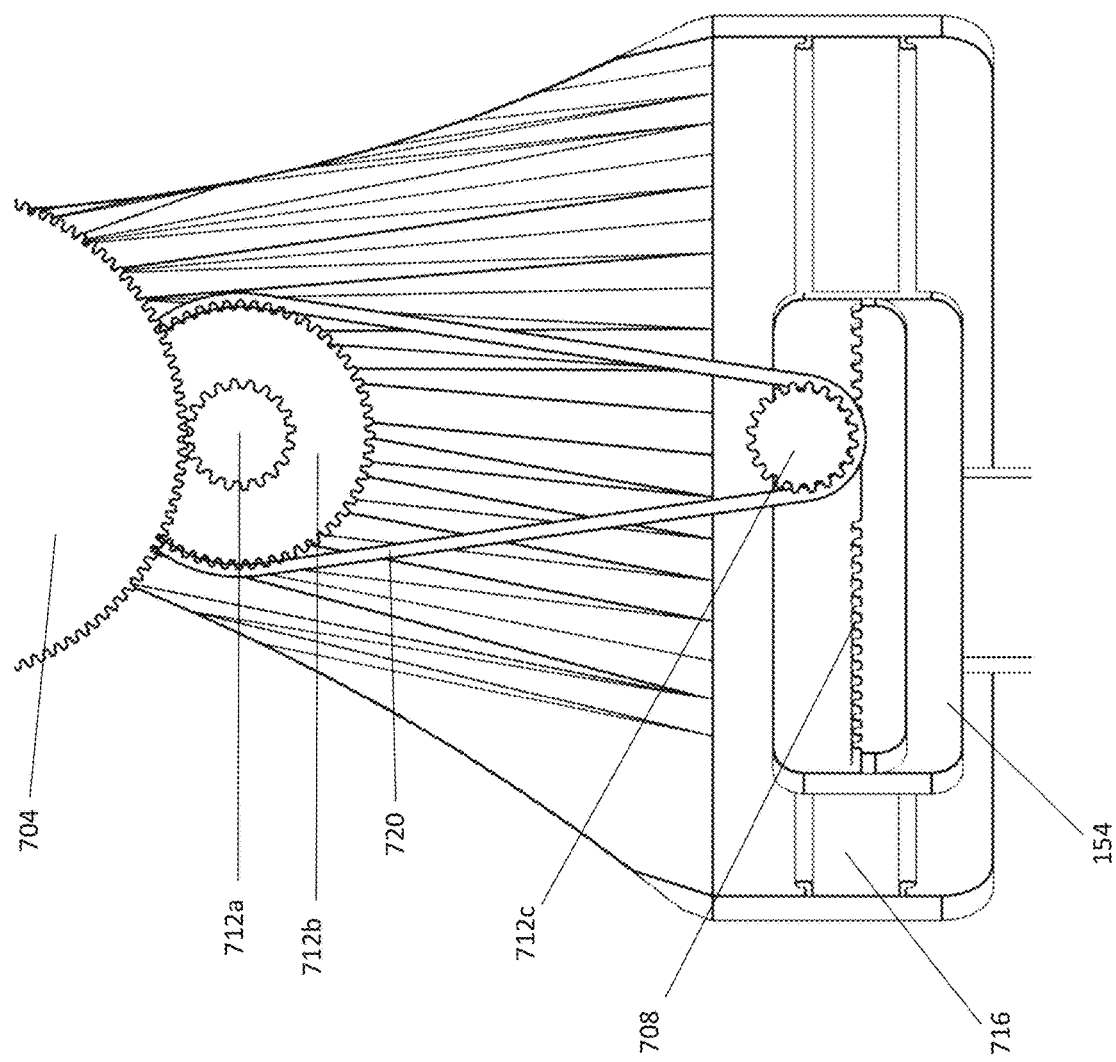
FIG. 22D depicts a side perspective view of another portion of the support member of FIG. 22A.
Figure 22E:
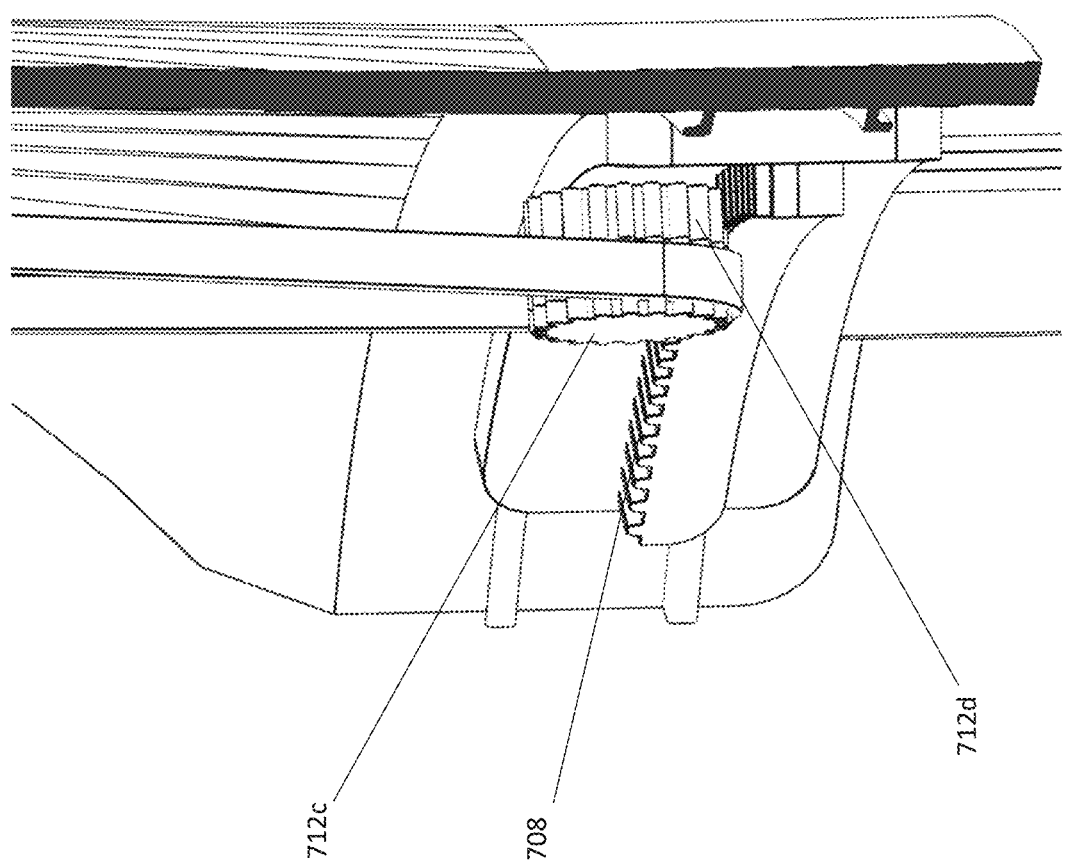
FIG. 22E depicts a side cross-sectional perspective view of another portion of the support member of FIG. 22A.
Figure 23:
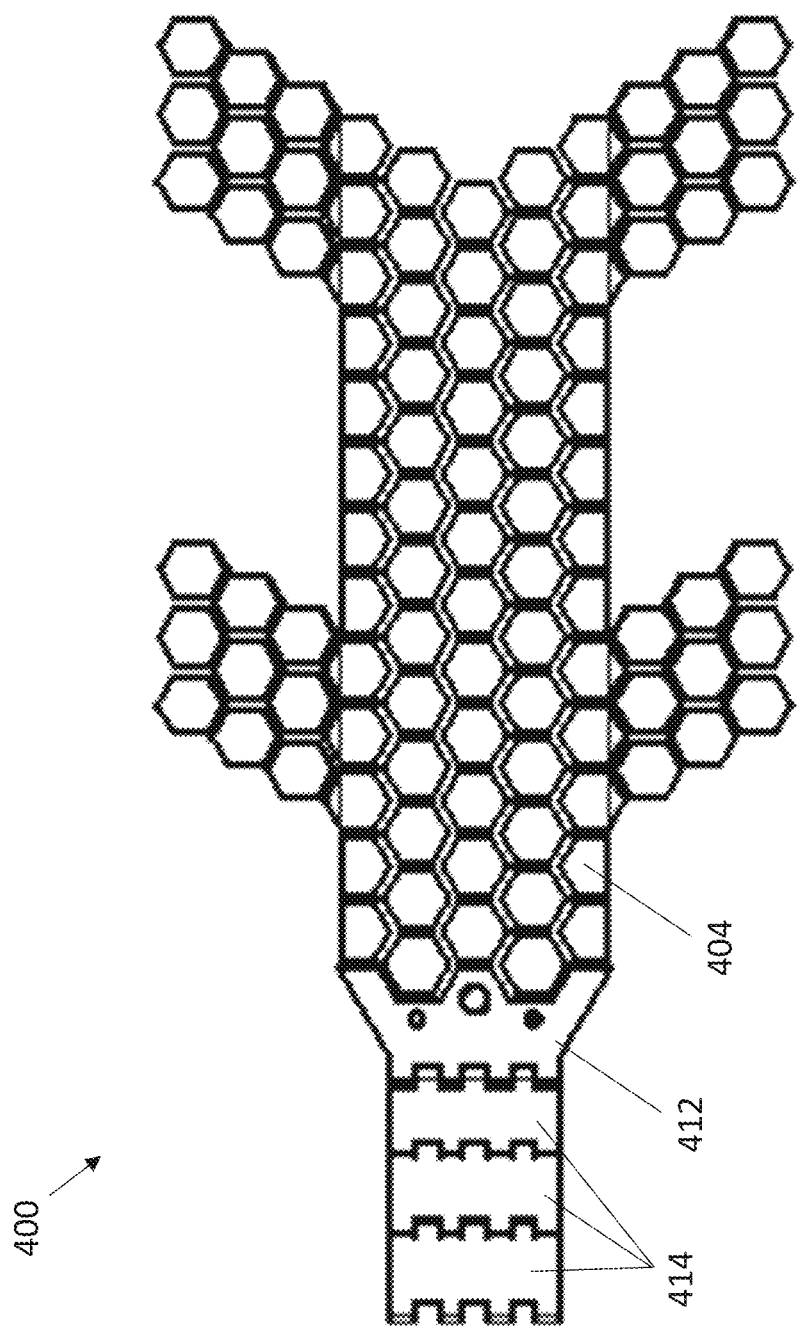
FIG. 23 depicts a side perspective view of a sleeve for a knee brace according to an aspect of the disclosure.
Figure 24:
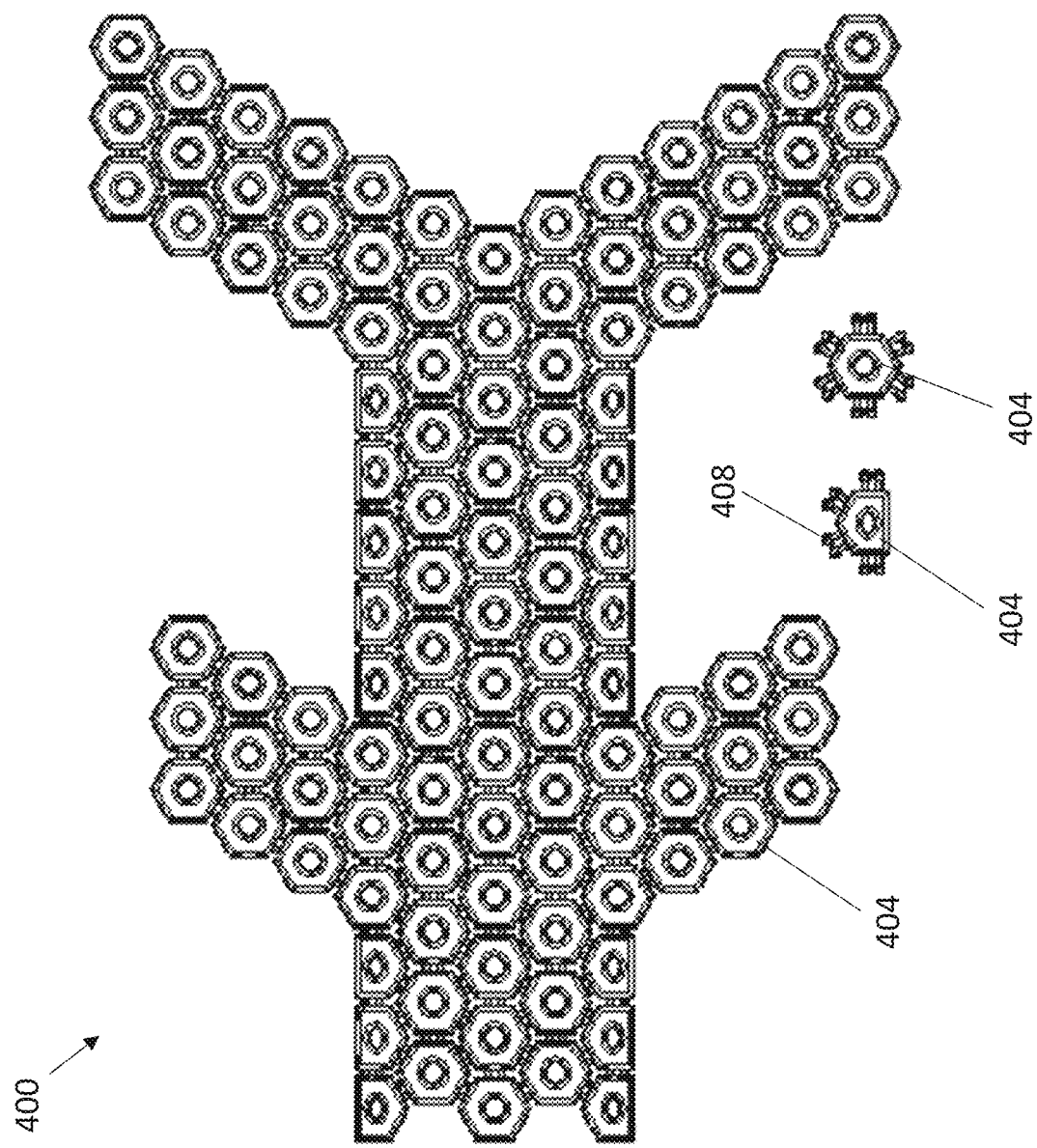
FIG. 24 depicts a side perspective view of a sleeve for a knee brace according to yet another aspect of the disclosure.
Figure 25:
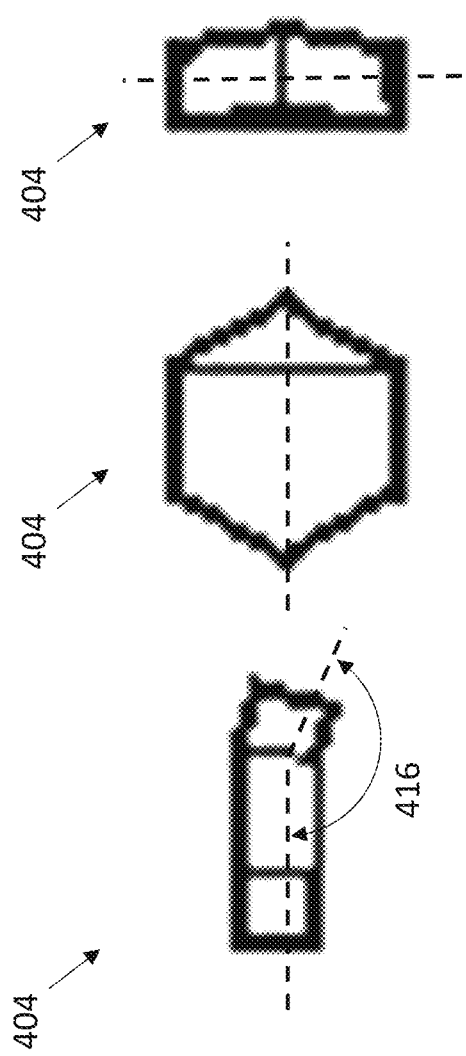
FIG. 25A depicts a front perspective view of a tile of a sleeve according to an aspect of the disclosure.
FIG. 25B depicts a side perspective view of the tile of FIG. 25A.
FIG. 25C depicts another side perspective view of the tile of FIG. 25A.

As shown in FIG. 22C, the pin 184 of the support module 700 may include a plurality of pins 184 disposed in the recess 188. A first pin 184a may be operatively coupled to the second pin 184b and to a third pin 184c. The second pin 184b and the third pin 184c are configured to engage with and move along a rack having teeth 710 defined within the recess 188. In some aspects, the rack having teeth 710 may operate substantially the same as the teeth 308 described previously. The addition of the second pin 184b and the third pin 184c serves to reverse the rotational direction of the translation of the pin 184 within the recess 188 due to the rotation of the first pin 184a. The third pin 184c can be included solely for stability purposes and does not affect the direction of rotation or translation.

In the exemplary embodiments of support modules 500, 600, and 700 described above, the second body 150 may be configured to move within the channel 516, 616, and 717 (respective to each embodiment) along a predetermined path. The channel 516, 616, and 717 may be curved (when viewed in a plane defined by the lower transverse axis 32 and the lower sagittal axis 33). Such curvature can be seen, for example, in FIG. 22E. Movement of the second body 150 along the curved path of the channel 516, 616, 716 can achieve the desired axial rotation, around the lower sagittal axis 31, of the brace components to correspond to the natural axial rotation of the lower leg 4 relative to the upper leg 3 as described throughout this application. In some embodiments, one or more of the pinions described with respect to support modules 500, 600, and/or 700 may be configured to selectively be engaged with, or selectively be disengaged from, at least one other pinion or rack. The selective engagement and disengagement can occur in response to the position of the second body 150 relative to the first body 120 along the flexion-extension pathway (shown in FIG. 15). That is, the geared arrangement of the hinge 180 described in FIGS. 20A-22E allows for engagement of geared components at a predetermined position during knee flexion and extension.

The support modules 500, 600, and 700 can each comprise the lateral side or the medial side of the brace 10 (i.e. can each be configured such that they contact the lateral side 2a of the leg 2 or the medial side 2b of the leg 2). In some embodiments, the support modules 500 and 600 may be configured to be the lateral support modules of the brace 10, while the support module 700 may be the medial support module of the brace 10. As the brace 10 flexes or extends (i.e. as the flexion angle 40 increases or decreases) the plane in which the lower body 150 of the lateral support module (e.g. support module 500 or 600) is disposed (defined by the lower frontal axis 31 and the lower sagittal axis 33) is approximately parallel to a plane in which the lower body 150 of the medial support module (e.g. support module 700) is disposed.

Such arrangements of the brace 10 change from coplanar motion at the level of the joint space to a curved circumferential contour inferiorly at the level of the upper tibia. Anterior and posterior linear translation of the lower body 150 (along the lower sagittal axis 33) occurs with knee flexion in the coplanar portion of the brace 10. The gearing mechanism described above with respect to modules 500, 600, and 700 causes rotation of the respective module axially around the lower frontal axis 31. This follows the natural internal/external axial rotation of the knee. In some embodiments, it may be preferable to control the pivoting point for rotation to accommodate desired flexion-extension movement. The amount of rotation by adjusting the arrangement, positioning, size, and other parameters of the gears (i.e. the pinions and the racks) disclosed above.

Furthermore, the specific arrangement and quantity of engaging pinions and racks (including the first pinions 504, 604, 704, intermediary pinions 512, 612, 712, and racks 508, 608, and 708) can be used to control and attenuate the translational and rotational motion of the lower body 150 relative to the upper body 120 within the plane defined by the upper frontal and sagittal axes 21 and 22, as well as axial rotation of the lower body 150 relative to the upper body 120 around the lower frontal axis 31.

Although the figures and descriptions throughout this application show and describe the hinge 180 and its various components as being disposed on the side of the relevant support module that contacts the leg, it will be understood that some or all components that make up the disclosed hinges 180 may be disposed on the opposite side of the support module (i.e. the side that faces away from the leg).

Some of the advantages described throughout this application are achieved by ensuring that the disclosed braces 10 are comfortably and consistently attached to the wearer's leg 2. As briefly explained above, the brace 10 (i.e. each support module 100) can be removably coupled to the wearer's leg by a fastener 112. The brace 10 should be affixed to the leg 2 tightly enough that the brace 10 does not slip along the leg or rotated around the leg during use, but loose enough that the leg (including blood vessels and nerves) are not overly tightly constrained to cause pain, discomfort, or injury. In some embodiments, the fastener 112 may include a plurality of fastening elements. In some embodiments, the fastener 112 may include a sleeve 400 coupled adjacent to the brace 10, such that the sleeve 400 is disposed between at least a portion of the brace 10 and the leg 2. The sleeve 400 can allow for dynamic changes in the upper leg 3 and the lower leg 4 during normal movement by the wearer, such as expansion or contraction of the girth of the upper leg 3 and lower leg 4 due to muscle contraction during normal flexion and extension. The sleeve 400 may be flexible such that it can assume the contour shape of the wearer's leg 2 when applied thereto. The sleeve 400 may include a flexible configuration and a rigid configuration. In the flexible configuration, the sleeve 400 may be placed in contact with the wearer's leg 2 and moved so as to conform to the shape of the leg 2, for example, by wrapping a portion of the sleeve 400 around a portion of the upper leg 3, the lower leg 4, or both. In the rigid configuration, the sleeve 400 may be configured to resist bending within the plane defined by the upper sagittal axis 23 and the upper frontal axis 21 (when the sleeve 400 is attached to the upper leg 3) or by the lower sagittal axis 33 and the lower frontal axis 31 (when the sleeve 400 is attached to the lower leg 4).

The fastener 112 may further include components to secure the sleeve 400 to the leg of the wearer. In some embodiments, the sleeves 400 may be held against the lower leg 4 by traditional means, such as adjustable elastic bands, adjustable belt strap, hook-and-loop fasteners, or the like. The sleeve 400 may be formed of a deformable material. The sleeve 400 may conform to the differing amounts of musculature or adipose mass among different individuals without losing rigidity in the plane defined by the sagittal and frontal axes noted above. The sleeve 400 may help to keep the hinge 180 of the brace 10 properly aligned with the wearer's knee joint 5. It is preferred that the knee brace 10 is configured to correspond to the natural flexion-extension motions of a normal healthy knee throughout the entire range of motion of the knee joint 5. If the brace does not match the natural anatomical movements of the wearer's leg, the brace can apply undesired forces to the knee to move the upper and/or lower leg portions into alignment with the motion of the brace. This can cause the knee to move kinetically abnormally, which can lead to joint damage. Furthermore, if the motion of the knee brace does not complement the natural flexion-extension motion of the leg, the brace can repeatedly move out of position, causing discomfort and minimizing the benefits of the brace.

Referring to FIGS. 23-28, embodiments of the sleeve 400 are depicted. The sleeve 400 may be formed from a plurality of tiles 404 arranged in a predetermined pattern. Each tile 404 may be attached to at least one other tile 404. The tiles 404 may have a particular geometric shape, such as hexagonal, pentagonal, rectangular, trapezoidal, triangular, round, or another suitable shape. The plurality of tiles 404 may be all the same shape and dimensions, or tiles 404 may vary within the sleeve 400. The non-limiting embodiments depicted in FIGS. 23-28 show hexagonal and pentagonal tiles 404, but it will be understood that other arrangements and shapes may be utilized. Some or all of the tiles 404 within the sleeve 400 may be substantially flat. Alternatively, some or all of the tiles 404 may be curved or angled. FIGS. 25A-25C show an exemplary hexagonal tile 404. FIG. 25A shows a side view of the tile 404, showing an angle 416 that is measured between at least two portions of the single tile 404. FIG. 25B shows a front view of the tile 404. FIG. 25C shows another side view of the tile 404. In some embodiments, the angle 416 may be approximately 15 degrees, but it will be understood that the angle 416 can be any suitable angle so long as the plurality of tiles 404, and the sleeve 400, can conform to the curvature and circumference of the wearer's leg, for example the thigh (i.e. upper leg 3) or the shin (i.e. lower leg 4).

Figure 26:
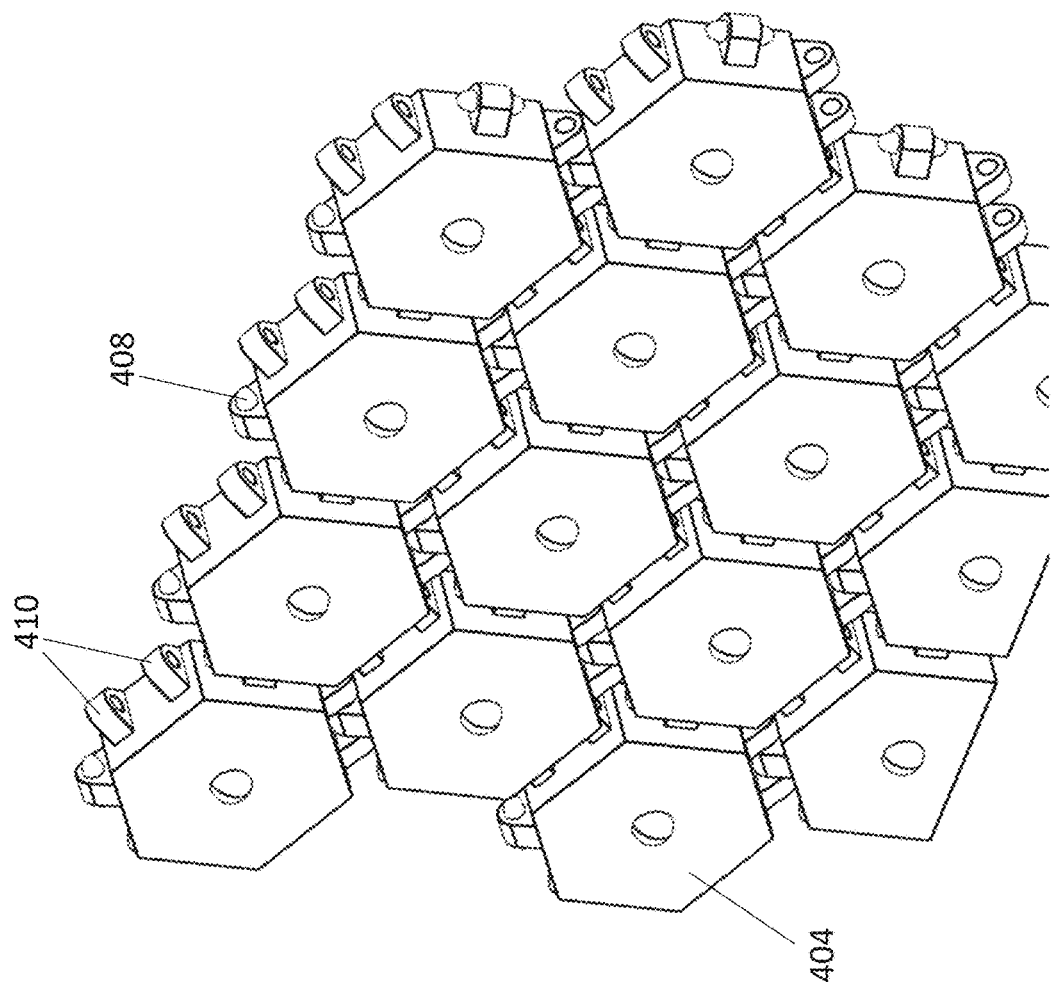
FIG. 26 depicts a plurality of tiles of a sleeve according to an aspect of the disclosure.
Figure 27:
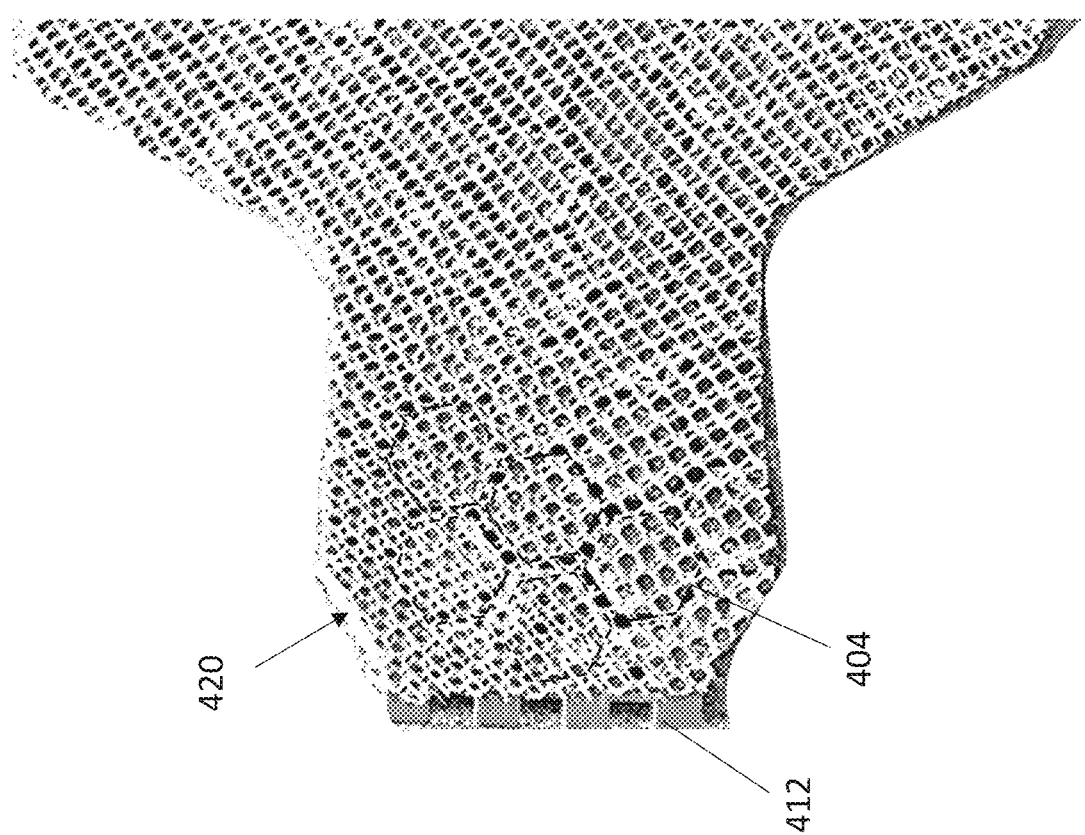
FIG. 27 depicts a sleeve for a knee brace according to yet another aspect of the disclosure.

Each tile 404 may be affixed to at least one other adjacent tile 404 via a fastening mechanism. Each tile 404 may include one or more components of the fastening mechanism, either as integral monolithic portions, or as separate components. The fastening mechanism may be a pin-and-socket mechanism. In some embodiments, one of the adjacent tiles 404 may include a pin 408 extending therefrom towards the other of the adjacent tiles 404, and the other of the adjacent tiles 404 may have a socket 410 defined thereon and configured to receive the pin 408 therein. In some embodiments, such as shown in FIG. 26, both adjacent tiles 404 may define respective sockets 410 thereon, and a separate pin 408 may be received into each socket 410, thus connecting the two adjacent tiles 404. The fastening mechanism (e.g. the pin 408 and socket 410) may allow movement in some or all directions. For example, when the sleeve 400 is engaged with the leg 2 of the wearer, the fastening mechanism may permit movement of adjacent tiles 404 relative to each other in directions parallel to the upper and/or lower transverse axes 22/32, while resisting relative movement in directions parallel to the upper and/or lower sagittal axes 23/33. In use, movement of the user or the user's leg can cause shifting of muscles of the upper leg 3 and/or the lower leg 4. In existing brace designs, such shifting can cause movement of the brace relative to the leg, changing the desired orientation or position of the brace relative to the leg. The sleeve 400 is configured to deform in response to the contraction of muscles or internal movement of muscles, bones, or other tissues, such that the brace 10 is not displaced due to such movement of the leg. For example, during inversion or eversion of the lower leg 4, connected muscle groups between the lower leg 4 and the upper leg 3 contract and change the circumferential shape of the lower leg 4 and the upper leg 3 where the brace 10 can attach. The sleeve 400 is configured to deform in response to such changes to prevent excessive undesired shifting of the brace 10.

The sleeve 400 may include a hinge 414 defined thereon (see FIG. 23) that is configured to removably couple the sleeve 400 to the brace 10. The sleeve 400 may include a plurality of hinges 414 coupled in series. The one or more hinges 414 are configured to fixedly attach to the first body 120 and/or to the second body 150, for example, at the respective necks 128 and 158. The one or more hinges 414 are connected to the rest of the sleeve 400 via an adapter 412 disposed between the one or more hinges 414 and the plurality of tiles 404. It will be appreciated that the sleeve 400 may include a plurality of adapters 412 and hinges 414 connected thereto, for example, separate adapters 412 and hinges 414 for at least one, or all, of: the neck 128 of the first body 120 of the lateral support module 100a, the neck 158 of the second body 150 of the lateral support module 100a, the neck 128 of the first body 120 of the medial support module 100b, and the neck 158 of the second body 150 of the medial support module 100b. The sleeve 400 may include a covering 420 configured to protect the tiles 404 and to provide physical support in one or more directions during use (see FIG. 27). The covering 420 may include fabric. In some embodiments, the covering 420 may include silicone. The covering 420 may be configured to be non-expansive or non-stretching in at least one direction. For example, the covering 420 may be configured to substantially resist stretching in directions within the plane defined by the upper and/or lower sagittal axes 23/33 and upper and/or lower frontal axes 21/31.

Figure 28:
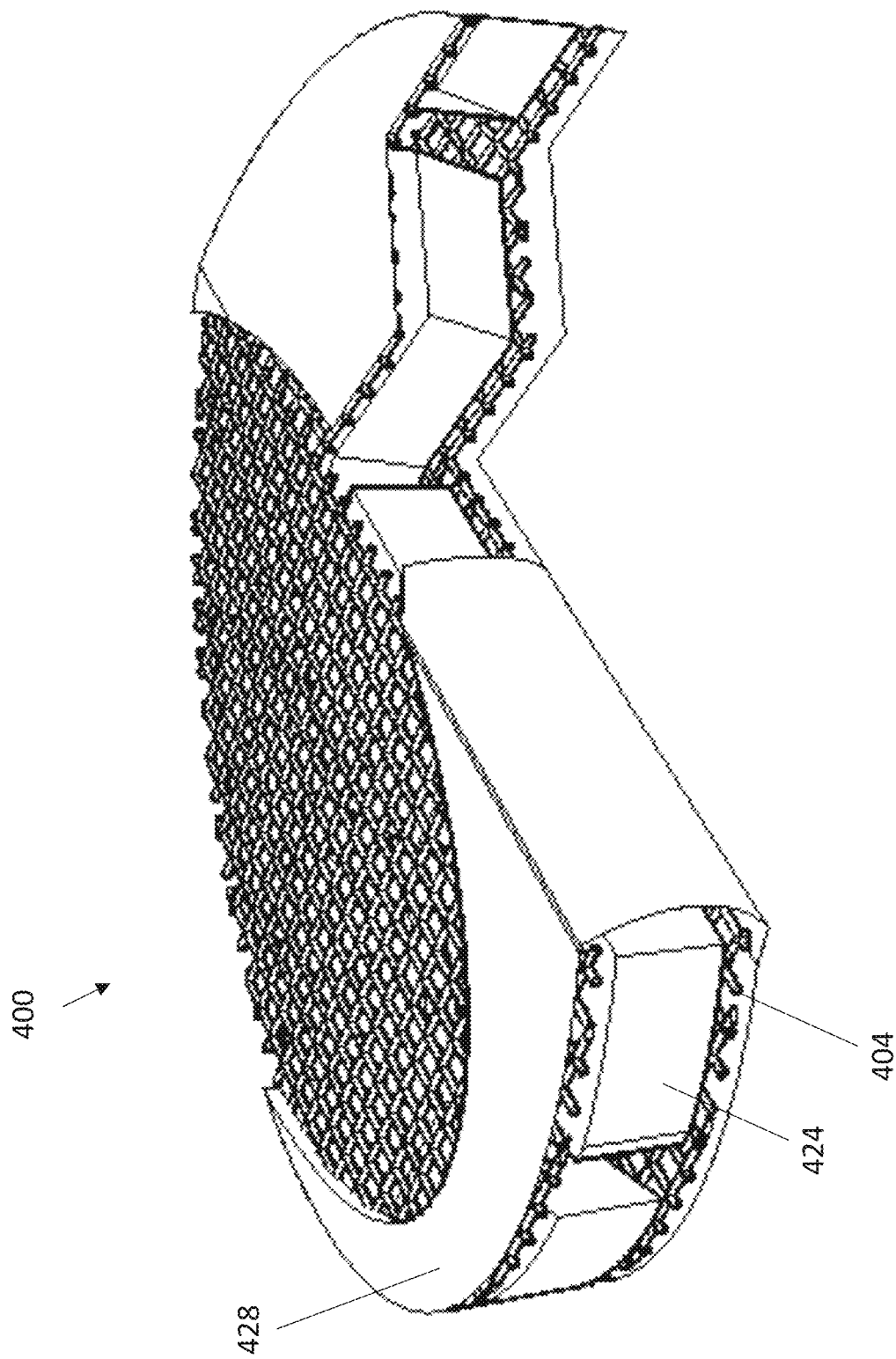
FIG. 28 depicts a sleeve for a knee brace according to yet another aspect of the disclosure.

In some embodiments, the sleeve 400 may be formed form a combination of layers of interconnected tiles 404 and other intermediate layers. Referring to FIG. 28, for example, one or more layers 424 may be arranged adjacent each other, with each layer 424 having a plurality of interconnected tiles 404. One or more coverings 420 may be arranged relative the one or more layers 424, for example, a covering 420 on one side of the one or more layers 424 and a covering 420 on the opposite side of the one or more layers 424, as shown in FIG. 28. In some embodiments, an external layer 428 may be disposed to encompass at least a portion of the sleeve 400. The external layer 428 may include a soft, tacky material configured to contact the wearer directly. The soft and tacky characteristics of the external layer 428 may help prevent migration of the sleeve 400 and/or the brace 10 along the skin surface of the wearer. The external layer 428 may include an anti-fungal material to resist fungal growth during wear.

It will be appreciated that there exist numerous variables that influence the specific rotation angles and translation distances of each support module 100 or 300 described throughout this application. The specific dimensions and shapes of components that comprise the disclosed embodiments of the brace 10 are dictated by these variables, which can differ between individuals. The disclosed embodiments are depicted with the intent to closely match normal human anatomy and kinesthesiological motion. It will be further understood that sizes, shapes, and relative orientation of components will also depend on the mobility, health, and size/shape of the wearer's leg 2 and knee joint 5.

Additional components may be introduced to facilitate coupling of the brace 10 to the leg 2 of the wearer, and/or to improve comfort. For example, in some embodiments, a side support, such as an air cushion 118 (see FIG. 8) may be disposed on the support module 100 adjacent the wearer's leg 2. The air cushion 118 is configured to pad the leg 2 against the relatively more rigid and harder materials of the rest of the support module 100. This can increase comfort for the wearer, minimize injury to soft tissue and neural structures, and decrease chance of migration or slipping of the brace 10 relative to the leg 2. The air cushion 118 can be made of a resilient material.

In some embodiments, the brace 10 may be configured to allow for limiting mobility along the flexion-extension pathway. For example, the brace 10 can be adjusted to allow only flexion-extension motion between two desired flexion angles 40. In some embodiments, the brace 10 can be adjusted to disallow any flexion-extension motion at all.

In use, the brace may be removably affixed to a wearer's leg 2 to provide support for the knee joint 5. The support module 100 may be coupled to the leg 2 via one or more fasteners 112. The fasteners 112 should sufficiently hold the support module 100 against the wearer's leg 2 such that the support module 100 is not loose or shifting from its desired position. The first body 120 can be coupled to the upper leg 3 of the wearer, and the second body 150 can be coupled to the lower leg 4 of the wearer. It will be appreciated that the arrangement can be reversed. If range of motion is desired to be inhibited or decreased, the support module 100 can be fixed such that the first body 120 cannot rotate relative to the second body 150 beyond the desired angle range. In some embodiments where the brace 10 includes two support modules 100, for example a lateral support module 100a and a medial support module 100b, both support modules 100a and 100b can be affixed to the wearer's leg 2. Additional components, for example, one or more sleeves 400, can be introduced to the brace 10 and/or the leg 2 of the wearer.

While systems and methods have been described in connection with the various embodiments of the various figures, it will be appreciated by those skilled in the art that changes could be made to the embodiments without departing from the broad inventive concept thereof. It is understood, therefore, that this disclosure is not limited to the particular embodiments disclosed, and it is intended to cover modifications within the spirit and scope of the present disclosure as defined by the claims.

When values are expressed as approximations by use of the antecedent "about" or "approximately," it will be understood that the particular value forms another embodiment. In general, use of the term "about" or "approximately" indicates approximations that can vary depending on the desired properties sought to be obtained by the disclosed subject matter and is to be interpreted in the specific context in which it is used, based on its function, and the person skilled in the art will be able to interpret it as such. Where present, all ranges are inclusive and combinable. That is, reference to values stated in ranges includes each and every value within that range.

What is claimed is:

1. A knee brace comprising:
    a support module comprising a first body, a second body, and a hinge movably coupling the first body to the second body, the hinge comprising:
        a pin on one of the first and second bodies,
        a receptacle defined by the other of the first and second bodies, the receptacle being configured to receive the pin therein, wherein the pin is rotatable and translatable within the receptacle, and
        a strut comprising a body including a first pin at one end and a second pin at another end opposite the one end, the first pin of the strut being received within a notch formed in the pin of the one of the first and second bodies, and the second pin of the strut being received within the other of the first and second bodies,
        wherein at least part of the body of the strut is received within a first curved notch formed in the pin of the one of the first and second bodies; and
    a fastener configured to releasably attach the knee brace to a leg,
    wherein one of the first and second bodies is configured to couple with a first portion of the leg via the fastener, and the other of the first and second bodies is configured to couple with a second portion of the leg via the fastener, the first and second portions of the leg being separated by a knee joint of the leg.

2. The knee brace of claim 1, wherein the support module is a first support module configured to contact a lateral side of the leg, the knee brace further comprising a second support module configured to contact a medial side of the leg, the second support module comprising a first body of the second support module, a second body of the second support module, and a hinge movably coupling the first body of the second support module to the second body of the second support module, the hinge of the second support module comprising:
    a pin on one of the first and second bodies of the second support module,
    a receptacle defined by the other of the first and second bodies of the second support module, the receptacle being configured to receive the pin of the second support module therein, wherein the pin of the second support module is rotatable and translatable within the receptacle of the second support module, and
    a strut comprising a body including a first pin at one end and a second pin at another end opposite the one end, the first pin of the strut of the second support module being received within a notch formed in the pin of the one of the first and second bodies of the second support module, and the second pin of the strut of the second support module being received within the other of the first and second bodies of the second support module,
    wherein at least part of the body of the strut of the hinge of the second support module is received within a curved notch formed in the pin of the one of the first and second bodies of the second support module.

3. The knee brace of claim 2, wherein the hinge of the first support module has:
    a first configuration in which the pin of the first support module is disposed at a first position within the receptacle of the first support module, and
    a second configuration in which the pin of the first support module is disposed at a second position within the receptacle of the first support module, the second position being rotationally and translationally offset from the first position.

4. The knee brace of claim 3, wherein, when the hinge of the first support module is transitioned from the first configuration to the second configuration, the pin of one of the first and second support modules is moved within the receptacle of the one of the first and second support modules by a first distance, and the pin of the other of the first and second support modules is moved within the receptacle of the other of the first and second support modules by a second distance, the first distance being different from the second distance.

5. The knee brace of claim 3, wherein, when the hinge of the first support module is transitioned from the first configuration to the second configuration:
    the second body of the first support module is configured to pivot relative to the first body of the first support module along a first axis,
    the second body of the first support module is configured to translate relative to the first body of the first support module at a first predetermined rate of distance per unit rotation,
    the second body of the second support module is configured to translate relative to the first body of the second support module at a second predetermined rate of distance per unit rotation, and
    the first and second predetermined rates are different from each other to cause the second portion of the leg to rotate about a second axis that is angularly offset from the first axis.

6. The knee brace of claim 2, wherein the first body of each of the first and second support modules is configured to be piboted around a first axis between 0 degrees and 150 degrees relative to the second body of each respective first and second support module.

7. The knee brace of claim 1, further comprising a sleeve disposed inside of the first and second bodies, the sleeve comprising a deformable material.

8. The knee brace of claim 7, wherein the sleeve comprises a plurality of tiles, wherein at least some of the plurality of tiles are movably coupled to each other.

9. The knee brace of claim 8, wherein at least some of the plurality of tiles are configured to be moved relative to each other in a first direction and configured to resist movement relative to each other in a second direction that is different from the first direction.

10. The knee brace of claim 1, wherein the receptacle is defined by a front wall, a rear wall opposite the front wall, a top wall, and a bottom wall opposite the top wall, the pin being configured to rotate and translate within the receptacle between the front, rear, top, and bottom walls.

11. The knee brace of claim 10, wherein the front wall of the receptacle is configured to contact the pin so as to prevent translational movement of the pin in a first direction, and the rear wall of the receptacle is configured to contact the pin so as to prevent translational movement of the pin in a second direction opposite the first direction.

12. The knee brace of claim 1, wherein the hinge further comprises a second strut comprising a first pin at one end and a second pin at another end opposite the one end, the first pin of the second strut being received within the one of the first and second bodies, and the second pin of the second strut being received within the other of the first and second bodies.

13. The knee brace of claim 12, wherein the hinge further comprises a second curved notch defined by the pin of the one of the first and second bodies, the second curved notch being configured to receive the second strut therein.

14. The knee brace of claim 1, wherein the first body is configured to be translated along the hinge for a distance between 0 mm and 40 mm relative to the second body.

15. The knee brace of claim 1, wherein the first body is configured to be pivoted around the hinge between 0 degrees and 150 degrees relative to the second body.

16. The knee brace of claim 1, wherein each of the first and second bodies defines inhibitor surfaces, wherein, when the inhibitor surfaces are in contact with each other, relative rotation between the first and second bodies is prevented in at least one rotational direction.

17. The knee brace of claim 1, wherein the second pin of the strut is received with another notch in the other of the first and second bodies.

18. The knee brace of claim 1 wherein the strut is configured to rotate at least partially relative to the pin about the first pin.

* * * * *